(12) United States Patent
Chen et al.

(10) Patent No.: US 7,435,818 B2
(45) Date of Patent: Oct. 14, 2008

(54) CRYSTAL FORMS OF IRINOTECAN HYDROCHLORIDE

(75) Inventors: Shu-Ping Chen, Kaohsiung (TW); Piin-Jye Harn, Tainan (TW)

(73) Assignee: Scinopharm Taiwan, Ltd., Tainan County (TW)

( * ) Notice: Subject to any disclaimer, the term of this patent is extended or adjusted under 35 U.S.C. 154(b) by 0 days.

(21) Appl. No.: 11/523,367

(22) Filed: Sep. 19, 2006

(65) Prior Publication Data

US 2007/0072890 A1 Mar. 29, 2007

Related U.S. Application Data

(60) Provisional application No. 60/718,827, filed on Sep. 20, 2005.

(51) Int. Cl.
*C07D 491/22* (2006.01)

(52) U.S. Cl. .......................................... 546/48; 546/47
(58) Field of Classification Search .................. 546/48, 546/47
See application file for complete search history.

(56) References Cited

U.S. PATENT DOCUMENTS

2006/0046993 A1 3/2006 Forino et al.

FOREIGN PATENT DOCUMENTS

WO WO 03/074527 9/2003
WO WO 2004/076460 9/2004

*Primary Examiner*—Charanjit S Aulakh
(74) *Attorney, Agent, or Firm*—Cohen Pontani Lieberman & Pavane LLP

(57) ABSTRACT

The present invention provides for novel crystalline forms of irinotecan hydrochloride and processes for their preparation, pharmaceutical compositions containing the novel forms and methods for treating metastatic carcinoma of the colon or rectum using same.

20 Claims, 20 Drawing Sheets

Fig. 1 (cont'd)

```
Comment:

Scan Type: Normal
Start Angle: 5 deg.
Stop Angle: 40 deg.
Num Points: 1751
Step Size: 0.02 deg.
Datafile Res: 1600
Scan Rate: 2.000000
Scan Mode: Continuous
Wavelength: 1.540562

Diffractometer Optics:
    Detector:
        Type: Fixed Slits
        X2 Configuration: No
    Tube:
        Type: Fixed Slits
        X2 Configuration: No
```

Peaks:

| Position (Deg.) | (Dsp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 12.3406 | 7.1665 | 0.0000 | 0.0000 | 1562.63 | 100.00 | 0.0600 | 0.0000 | 199.5 | PFind | None | 0.00 | 0.00 | None |
| 24.7913 | 3.5884 | 0.0000 | 0.0000 | 913.23 | 54.93 | 0.1200 | 0.0000 | 146.1 | PFind | None | 0.00 | 0.00 | None |
| 10.9438 | 8.0779 | 0.0000 | 0.0000 | 891.13 | 53.60 | 0.1400 | 0.0000 | 124.8 | PFind | None | 0.00 | 0.00 | None |
| 8.2056 | 10.7862 | 0.0000 | 0.0000 | 762.43 | 45.86 | 0.1200 | 0.0000 | 91.5 | PFind | None | 0.00 | 0.00 | None |
| 27.6750 | 3.2207 | 0.0000 | 0.0000 | 663.63 | 39.91 | 0.1200 | 0.0000 | 92.9 | PFind | None | 0.00 | 0.00 | None |
| 22.7206 | 3.9105 | 0.0000 | 0.0000 | 648.02 | 38.98 | 0.1600 | 0.0000 | 77.8 | PFind | None | 0.00 | 0.00 | None |
| 21.2350 | 4.1806 | 0.0000 | 0.0000 | 619.23 | 37.24 | 0.1200 | 0.0000 | 86.7 | PFind | None | 0.00 | 0.00 | None |
| 20.9744 | 4.2319 | 0.0000 | 0.0000 | 541.27 | 32.55 | 0.1600 | 0.0000 | 86.6 | PFind | None | 0.00 | 0.00 | None |
| 20.6731 | 4.2929 | 0.0000 | 0.0000 | 531.53 | 31.97 | 0.0600 | 0.0000 | 85.0 | PFind | None | 0.00 | 0.00 | None |
| 14.3263 | 6.1773 | 0.0000 | 0.0000 | 520.45 | 31.30 | 0.1200 | 0.0000 | 62.5 | PFind | None | 0.00 | 0.00 | None |
| 25.9806 | 3.4267 | 0.0000 | 0.0000 | 519.83 | 31.27 | 0.1400 | 0.0000 | 83.2 | PFind | None | 0.00 | 0.00 | None |
| 19.9800 | 4.4403 | 0.0000 | 0.0000 | 471.90 | 28.38 | 0.0400 | 0.0000 | 75.5 | PFind | None | 0.00 | 0.00 | None |
| 21.9256 | 4.0504 | 0.0000 | 0.0000 | 370.20 | 22.27 | 0.0400 | 0.0000 | 51.8 | PFind | None | 0.00 | 0.00 | None |
| 16.0081 | 5.5319 | 0.0000 | 0.0000 | 306.25 | 18.42 | 0.0800 | 0.0000 | 42.9 | PFind | None | 0.00 | 0.00 | None |
| 12.5813 | 7.0299 | 0.0000 | 0.0000 | 282.90 | 17.02 | 0.0200 | 0.0000 | 45.3 | PFind | None | 0.00 | 0.00 | None |
| 15.8125 | 5.5999 | 0.0000 | 0.0000 | 267.68 | 16.10 | 0.1200 | 0.0000 | 32.1 | PFind | None | 0.00 | 0.00 | None |
| 9.4925 | 9.3093 | 0.0000 | 0.0000 | 233.87 | 14.07 | 0.1400 | 0.0000 | 23.4 | PFind | None | 0.00 | 0.00 | None |
| 18.6344 | 4.7578 | 0.0000 | 0.0000 | 228.47 | 13.74 | 0.1600 | 0.0000 | 27.4 | PFind | None | 0.00 | 0.00 | None |
| 30.4600 | 2.9322 | 0.0000 | 0.0000 | 226.67 | 13.63 | 0.1600 | 0.0000 | 36.3 | PFind | None | 0.00 | 0.00 | None |
| 16.5000 | 5.3681 | 0.0000 | 0.0000 | 216.67 | 13.03 | 0.1600 | 0.0000 | 8.7 | PFind | None | 0.00 | 0.00 | None |
| 24.2969 | 3.6602 | 0.0000 | 0.0000 | 212.90 | 12.80 | 0.1400 | 0.0000 | 17.0 | PFind | None | 0.00 | 0.00 | None |
| 29.4063 | 3.0349 | 0.0000 | 0.0000 | 212.77 | 12.80 | 0.1200 | 0.0000 | 34.0 | PFind | None | 0.00 | 0.00 | None |
| 30.4231 | 2.9357 | 0.0000 | 0.0000 | 210.72 | 12.67 | 0.1200 | 0.0000 | 33.7 | PFind | None | 0.00 | 0.00 | None |
| 19.0400 | 4.6573 | 0.0000 | 0.0000 | 202.63 | 12.19 | 0.0800 | 0.0000 | 28.4 | PFind | None | 0.00 | 0.00 | None |
| 27.8969 | 3.1955 | 0.0000 | 0.0000 | 159.52 | 9.59 | 0.0800 | 0.0000 | 19.1 | PFind | None | 0.00 | 0.00 | None |
| 28.8956 | 3.0873 | 0.0000 | 0.0000 | 152.10 | 9.15 | 0.1600 | 0.0000 | 24.3 | PFind | None | 0.00 | 0.00 | None |
| 17.1669 | 5.1610 | 0.0000 | 0.0000 | 141.23 | 8.49 | 0.0200 | 0.0000 | 11.3 | PFind | None | 0.00 | 0.00 | None |
| 28.6806 | 3.1100 | 0.0000 | 0.0000 | 131.32 | 7.90 | 0.1600 | 0.0000 | 18.4 | PFind | None | 0.00 | 0.00 | None |
| 16.7000 | 5.3042 | 0.0000 | 0.0000 | 108.33 | 6.52 | 0.0200 | 0.0000 | 4.3 | PFind | None | 0.00 | 0.00 | None |
| 7.5000 | 11.7774 | 0.0000 | 0.0000 | 106.67 | 6.42 | 0.0800 | 0.0000 | 6.4 | PFind | None | 0.00 | 0.00 | None |
| 15.5369 | 5.6986 | 0.0000 | 0.0000 | 100.30 | 6.03 | 0.1400 | 0.0000 | 6.0 | PFind | None | 0.00 | 0.00 | None |
| 26.6400 | 3.3434 | 0.0000 | 0.0000 | 100.00 | 6.01 | 0.1200 | 0.0000 | 2.0 | PFind | None | 0.00 | 0.00 | None |
| 23.5500 | 3.7730 | 0.0000 | 0.0000 | 96.67 | 5.81 | 0.0200 | 0.0000 | 7.7 | PFind | None | 0.00 | 0.00 | None |
| 14.6081 | 6.0588 | 0.0000 | 0.0000 | 89.20 | 5.36 | 0.1600 | 0.0000 | 14.3 | PFind | None | 0.00 | 0.00 | None |
| 27.1688 | 3.2795 | 0.0000 | 0.0000 | 89.18 | 5.36 | 0.0200 | 0.0000 | 7.1 | PFind | None | 0.00 | 0.00 | None |
| 31.2600 | 2.8590 | 0.0000 | 0.0000 | 76.67 | 4.61 | 0.1400 | 0.0000 | 0.0 | PFind | None | 0.00 | 0.00 | None |
| 25.3600 | 3.5092 | 0.0000 | 0.0000 | 75.00 | 4.51 | 0.1600 | 0.0000 | 1.5 | PFind | None | 0.00 | 0.00 | None |
| 17.6200 | 5.0293 | 0.0000 | 0.0000 | 75.00 | 4.51 | 0.0000 | 0.0000 | 1.5 | PFind | None | 0.00 | 0.00 | None |

FIG. 2 (cont'd)

| Position: | 1451.69 | Intensity: | 30.084 |
|---|---|---|---|
| Position: | 1231.40 | Intensity: | 30.013 |
| Position: | 1216.96 | Intensity: | 30.651 |
| Position: | 1435.03 | Intensity: | 30.898 |
| Position: | 1160.17 | Intensity: | 30.746 |
| Position: | 3371.83 | Intensity: | 36.755 |
| Position: | 1418.44 | Intensity: | 37.482 |
| Position: | 1566.56 | Intensity: | 38.571 |
| Position: | 1107.45 | Intensity: | 41.883 |
| Position: | 1007.27 | Intensity: | 42.008 |
| Position: | 1065.83 | Intensity: | 42.439 |
| Position: | 1129.50 | Intensity: | 43.672 |
| Position: | 1077.99 | Intensity: | 43.892 |
| Position: | 2942.34 | Intensity: | 44.143 |
| Position: | 1359.31 | Intensity: | 44.431 |
| Position: | 2545.69 | Intensity: | 45.507 |
| Position: | 2968.11 | Intensity: | 45.922 |
| Position: | 1280.24 | Intensity: | 46.495 |
| Position: | 3516.52 | Intensity: | 47.235 |
| Position: | 2829.28 | Intensity: | 47.689 |
| Position: | 1334.30 | Intensity: | 48.098 |
| Position: | 746.43 | Intensity: | 48.121 |
| Position: | 1511.28 | Intensity: | 48.277 |
| Position: | 849.19 | Intensity: | 48.631 |
| Position: | 1039.05 | Intensity: | 49.667 |
| Position: | 2851.85 | Intensity: | 50.967 |
| Position: | 567.12 | Intensity: | 51.327 |
| Position: | 587.67 | Intensity: | 52.185 |
| Position: | 1302.89 | Intensity: | 52.261 |
| Position: | 534.85 | Intensity: | 52.384 |
| Position: | 725.56 | Intensity: | 52.727 |
| Position: | 810.22 | Intensity: | 53.350 |
| Position: | 671.16 | Intensity: | 53.494 |
| Position: | 406.69 | Intensity: | 53.947 |
| Position: | 2878.50 | Intensity: | 55.419 |
| Position: | 401.13 | Intensity: | 55.591 |
| Position: | 436.10 | Intensity: | 57.018 |
| Position: | 955.95 | Intensity: | 57.045 |
| Position: | 879.94 | Intensity: | 57.262 |
| Position: | 486.55 | Intensity: | 57.342 |
| Position: | 837.51 | Intensity: | 57.445 |
| Position: | 784.33 | Intensity: | 57.911 |
| Position: | 825.93 | Intensity: | 58.820 |

FIG. 2 (cont'd)

| | | | |
|---|---|---|---|
| Position: | 460.91 | Intensity: | 59.478 |
| Position: | 495.78 | Intensity: | 60.576 |
| Position: | 421.39 | Intensity: | 60.054 |
| Position: | 920.00 | Intensity: | 61.433 |
| Position: | 414.68 | Intensity: | 64.633 |
| Position: | 448.78 | Intensity: | 70.735 |

Fig 3 (cont'd)

Comment:

Scan Type: Normal
Start Angle: 5 deg.
Stop Angle: 40 deg.
Num Points: 1751
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | Position (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 20.3956 | 4.3507 | 0.0000 | 0.0000 | 746.23 | 100.00 | 0.1200 | 0.0000 | 89.5 | PFind | None | 0.00 | 0.00 | None |
| 22.2950 | 3.9842 | 0.0000 | 0.0000 | 719.65 | 96.44 | 0.1100 | 0.0000 | 100.8 | PFind | None | 0.00 | 0.00 | None |
| 12.0744 | 7.3239 | 0.0000 | 0.0000 | 428.83 | 57.47 | 0.1600 | 0.0000 | 68.6 | PFind | None | 0.00 | 0.00 | None |
| 8.4800 | 10.4184 | 0.0000 | 0.0000 | 396.32 | 53.11 | 0.1600 | 0.0000 | 55.5 | PFind | None | 0.00 | 0.00 | None |
| 11.8306 | 7.4742 | 0.0000 | 0.0000 | 381.37 | 51.11 | 0.1600 | 0.0000 | 61.0 | PFind | None | 0.00 | 0.00 | None |
| 15.7587 | 5.6189 | 0.0000 | 0.0000 | 319.98 | 42.88 | 0.1000 | 0.0000 | 51.2 | PFind | None | 0.00 | 0.00 | None |
| 18.5200 | 4.7869 | 0.0000 | 0.0000 | 301.87 | 40.45 | 0.1500 | 0.0000 | 48.3 | PFind | None | 0.00 | 0.00 | None |
| 24.2925 | 3.6609 | 0.0000 | 0.0000 | 272.73 | 36.55 | 0.1600 | 0.0000 | 43.6 | PFind | None | 0.00 | 0.00 | None |
| 23.6644 | 3.7566 | 0.0000 | 0.0000 | 264.98 | 35.51 | 0.1200 | 0.0000 | 31.8 | PFind | None | 0.00 | 0.00 | None |
| 6.9050 | 12.7909 | 0.0000 | 0.0000 | 264.53 | 35.45 | 0.0400 | 0.0000 | 31.7 | PFind | None | 0.00 | 0.00 | None |
| 29.0012 | 3.0763 | 0.0000 | 0.0000 | 264.43 | 35.44 | 0.1600 | 0.0000 | 42.3 | PFind | None | 0.00 | 0.00 | None |
| 17.1800 | 5.1571 | 0.0000 | 0.0000 | 251.67 | 33.72 | 0.0400 | 0.0000 | 10.1 | PFind | None | 0.00 | 0.00 | None |
| 13.4800 | 6.5632 | 0.0000 | 0.0000 | 220.00 | 29.48 | 0.1200 | 0.0000 | 22.0 | PFind | None | 0.00 | 0.00 | None |
| 30.8400 | 2.8970 | 0.0000 | 0.0000 | 215.00 | 28.81 | 0.0400 | 0.0000 | 12.9 | PFind | None | 0.00 | 0.00 | None |
| 27.9700 | 3.1874 | 0.0000 | 0.0000 | 215.00 | 28.81 | 0.0600 | 0.0000 | 30.1 | PFind | None | 0.00 | 0.00 | None |
| 25.3463 | 3.5110 | 0.0000 | 0.0000 | 204.68 | 27.43 | 0.0400 | 0.0000 | 24.6 | PFind | None | 0.00 | 0.00 | None |
| 26.4425 | 3.3679 | 0.0000 | 0.0000 | 186.97 | 25.05 | 0.1200 | 0.0000 | 22.4 | PFind | None | 0.00 | 0.00 | None |
| 27.1200 | 3.2853 | 0.0000 | 0.0000 | 186.67 | 25.01 | 0.0200 | 0.0000 | 11.2 | PFind | None | 0.00 | 0.00 | None |
| 28.7288 | 3.1049 | 0.0000 | 0.0000 | 180.95 | 24.25 | 0.0200 | 0.0000 | 29.0 | PFind | None | 0.00 | 0.00 | None |
| 14.7000 | 6.0211 | 0.0000 | 0.0000 | 175.00 | 23.45 | 0.1200 | 0.0000 | 17.5 | PFind | None | 0.00 | 0.00 | None |
| 17.0069 | 5.2092 | 0.0000 | 0.0000 | 168.02 | 22.52 | 0.1400 | 0.0000 | 20.2 | PFind | None | 0.00 | 0.00 | None |
| 25.1200 | 3.5421 | 0.0000 | 0.0000 | 160.00 | 21.44 | 0.1200 | 0.0000 | 9.6 | PFind | None | 0.00 | 0.00 | None |
| 19.6200 | 4.5209 | 0.0000 | 0.0000 | 145.00 | 19.43 | 0.0800 | 0.0000 | 5.8 | PFind | None | 0.00 | 0.00 | None |
| 21.8931 | 4.0564 | 0.0000 | 0.0000 | 143.75 | 19.26 | 0.1200 | 0.0000 | 17.3 | PFind | None | 0.00 | 0.00 | None |
| 10.1350 | 8.7206 | 0.0000 | 0.0000 | 138.58 | 18.57 | 0.1600 | 0.0000 | 22.2 | PFind | None | 0.00 | 0.00 | None |
| 25.9400 | 3.4320 | 0.0000 | 0.0000 | 135.00 | 18.09 | 0.0600 | 0.0000 | 0.0 | PFind | None | 0.00 | 0.00 | None |
| 23.1906 | 3.8323 | 0.0000 | 0.0000 | 129.67 | 17.38 | 0.1200 | 0.0000 | 10.4 | PFind | None | 0.00 | 0.00 | None |
| 15.3200 | 5.7786 | 0.0000 | 0.0000 | 120.00 | 16.08 | 0.0600 | 0.0000 | 4.8 | PFind | None | 0.00 | 0.00 | None |
| 29.5600 | 3.0194 | 0.0000 | 0.0000 | 115.00 | 15.41 | 0.0000 | 0.0000 | 0.0 | PFind | None | 0.00 | 0.00 | None |
| 25.7600 | 3.4556 | 0.0000 | 0.0000 | 111.67 | 14.96 | 0.1200 | 0.0000 | 6.7 | PFind | None | 0.00 | 0.00 | None |
| 18.0231 | 4.9177 | 0.0000 | 0.0000 | 107.30 | 14.38 | 0.0600 | 0.0000 | 12.9 | PFind | None | 0.00 | 0.00 | None |
| 31.4550 | 2.8417 | 0.0000 | 0.0000 | 106.40 | 14.26 | 0.1400 | 0.0000 | 14.9 | PFind | None | 0.00 | 0.00 | None |
| 20.9400 | 4.2388 | 0.0000 | 0.0000 | 103.33 | 13.85 | 0.0200 | 0.0000 | 2.1 | PFind | None | 0.00 | 0.00 | None |
| 19.0000 | 4.6670 | 0.0000 | 0.0000 | 101.67 | 13.62 | 0.1600 | 0.0000 | 6.1 | PFind | None | 0.00 | 0.00 | None |
| 33.1600 | 2.6994 | 0.0000 | 0.0000 | 100.00 | 13.40 | 0.0800 | 0.0000 | 8.0 | PFind | None | 0.00 | 0.00 | None |
| 23.0400 | 3.8570 | 0.0000 | 0.0000 | 100.00 | 13.40 | 0.1200 | 0.0000 | 12.0 | PFind | None | 0.00 | 0.00 | None |
| 15.5200 | 5.8165 | 0.0000 | 0.0000 | 81.67 | 10.94 | 0.0000 | 0.0000 | 3.3 | PFind | None | 0.00 | 0.00 | None |
| 30.7000 | 2.9099 | 0.0000 | 0.0000 | 80.42 | 10.78 | 0.0600 | 0.0000 | 6.4 | PFind | None | 0.00 | 0.00 | None |
| 21.2600 | 4.1757 | 0.0000 | 0.0000 | 78.33 | 10.50 | 0.1400 | 0.0000 | 1.6 | PFind | None | 0.00 | 0.00 | None |
| 30.4000 | 2.9379 | 0.0000 | 0.0000 | 71.67 | 9.60 | 0.0800 | 0.0000 | 5.7 | PFind | None | 0.00 | 0.00 | None |

Fig. 5 cont'd

```
Comment:

Scan Type: Normal
Start Angle: 5 deg.
Stop Angle: 40 deg.
Num Points: 1751
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    K2 Configuration: No
  Tube:
    Type: Fixed Slits
    K2 Configuration: No
```

Peaks:

| Position (Deg.) | d (Dsp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 23.9600 | 3.7109 | 0.0000 | 0.0000 | 421.67 | 100.00 | 0.1400 | 0.0000 | 59.0 | PFind | None | 0.00 | 0.00 | None |
| 20.9200 | 4.2428 | 0.0000 | 0.0000 | 365.00 | 86.56 | 0.0200 | 0.0000 | 58.4 | PFind | None | 0.00 | 0.00 | None |
| 21.0800 | 4.2110 | 0.0000 | 0.0000 | 331.67 | 78.66 | 0.0400 | 0.0000 | 53.1 | PFind | None | 0.00 | 0.00 | None |
| 21.0944 | 4.2081 | 0.0000 | 0.0000 | 308.53 | 73.17 | 0.0400 | 0.0000 | 49.4 | PFind | None | 0.00 | 0.00 | None |
| 23.8375 | 3.7297 | 0.0000 | 0.0000 | 295.17 | 70.00 | 0.0200 | 0.0000 | 41.3 | PFind | None | 0.00 | 0.00 | None |
| 24.3200 | 3.6568 | 0.0000 | 0.0000 | 236.33 | 56.13 | 0.0400 | 0.0000 | 9.5 | PFind | None | 0.00 | 0.00 | None |
| 10.2800 | 8.5979 | 0.0000 | 0.0000 | 153.33 | 36.36 | 0.0200 | 0.0000 | 6.1 | PFind | None | 0.00 | 0.00 | None |
| 24.4800 | 3.6333 | 0.0000 | 0.0000 | 143.33 | 33.99 | 0.0400 | 0.0000 | 5.7 | PFind | None | 0.00 | 0.00 | None |
| 9.5800 | 10.2972 | 0.0000 | 0.0000 | 138.33 | 32.81 | 0.0200 | 0.0000 | 2.8 | PFind | None | 0.00 | 0.00 | None |
| 8.4200 | 10.4925 | 0.0000 | 0.0000 | 136.67 | 32.41 | 0.0600 | 0.0000 | 19.1 | PFind | None | 0.00 | 0.00 | None |
| 24.6600 | 3.6072 | 0.0000 | 0.0000 | 130.00 | 30.83 | 0.1600 | 0.0000 | 5.2 | PFind | None | 0.00 | 0.00 | None |
| 24.9000 | 3.5729 | 0.0000 | 0.0000 | 128.33 | 30.43 | 0.1600 | 0.0000 | 7.7 | PFind | None | 0.00 | 0.00 | None |
| 26.0000 | 3.4242 | 0.0000 | 0.0000 | 126.67 | 30.04 | 0.1400 | 0.0000 | 0.0 | PFind | None | 0.00 | 0.00 | None |
| 10.1600 | 8.6992 | 0.0000 | 0.0000 | 126.67 | 30.04 | 0.1400 | 0.0000 | 5.1 | PFind | None | 0.00 | 0.00 | None |
| 20.1600 | 4.4010 | 0.0000 | 0.0000 | 120.00 | 28.46 | 0.0400 | 0.0000 | 0.0 | PFind | None | 0.00 | 0.00 | None |
| 26.2400 | 3.3934 | 0.0000 | 0.0000 | 118.33 | 28.06 | 0.0200 | 0.0000 | 2.4 | PFind | None | 0.00 | 0.00 | None |
| 25.2056 | 3.5303 | 0.0000 | 0.0000 | 113.45 | 26.91 | 0.0400 | 0.0000 | 6.8 | PFind | None | 0.00 | 0.00 | None |
| 20.2400 | 4.3838 | 0.0000 | 0.0000 | 103.33 | 24.51 | 0.0400 | 0.0000 | 4.1 | PFind | None | 0.00 | 0.00 | None |
| 20.4600 | 4.3372 | 0.0000 | 0.0000 | 98.33 | 23.32 | 0.0600 | 0.0000 | 7.9 | PFind | None | 0.00 | 0.00 | None |
| 25.4600 | 3.4956 | 0.0000 | 0.0000 | 98.33 | 23.32 | 0.0800 | 0.0000 | 7.9 | PFind | None | 0.00 | 0.00 | None |
| 25.6800 | 3.4768 | 0.0000 | 0.0000 | 96.67 | 22.92 | 0.0800 | 0.0000 | 3.9 | PFind | None | 0.00 | 0.00 | None |
| 26.0400 | 3.3189 | 0.0000 | 0.0000 | 83.33 | 19.76 | 0.0400 | 0.0000 | 1.7 | PFind | None | 0.00 | 0.00 | None |
| 17.1000 | 5.1811 | 0.0000 | 0.0000 | 71.67 | 17.00 | 0.0000 | 0.0000 | 2.9 | PFind | None | 0.00 | 0.00 | None |
| 16.7800 | 5.2791 | 0.0000 | 0.0000 | 71.67 | 17.00 | 0.0200 | 0.0000 | 1.4 | PFind | None | 0.00 | 0.00 | None |
| 35.6800 | 2.5007 | 0.0000 | 0.0000 | 70.00 | 16.60 | 0.0200 | 0.0000 | 1.4 | PFind | None | 0.00 | 0.00 | None |
| 30.4400 | 2.9341 | 0.0000 | 0.0000 | 68.33 | 14.21 | 0.0200 | 0.0000 | 1.1 | PFLnd | None | 0.00 | 0.00 | None |
| 29.1000 | 3.0661 | 0.0000 | 0.0000 | 66.67 | 15.81 | 0.0200 | 0.0000 | 1.1 | PFind | None | 0.00 | 0.00 | None |
| 17.0200 | 5.2052 | 0.0000 | 0.0000 | 66.67 | 15.81 | 0.0200 | 0.0000 | 1.3 | PFind | None | 0.00 | 0.00 | None |

Fig. 6 (cnt'd)

| | | | |
|---|---|---|---|
| Position: | 1010.90 | Intensity: | 53.582 |
| Position: | 1032.14 | Intensity: | 55.258 |
| Position: | 1056.53 | Intensity: | 55.827 |
| Position: | 2939.41 | Intensity: | 56.448 |
| Position: | 1108.89 | Intensity: | 57.364 |
| Position: | 1278.36 | Intensity: | 59.259 |
| Position: | 420.21 | Intensity: | 59.261 |
| Position: | 409.12 | Intensity: | 59.320 |
| Position: | 1330.74 | Intensity: | 61.341 |
| Position: | 3356.90 | Intensity: | 61.718 |
| Position: | 1510.95 | Intensity: | 62.420 |
| Position: | 1364.87 | Intensity: | 63.220 |
| Position: | 2873.91 | Intensity: | 63.377 |
| Position: | 401.13 | Intensity: | 63.830 |
| Position: | 491.17 | Intensity: | 63.813 |
| Position: | 508.73 | Intensity: | 63.948 |
| Position: | 562.60 | Intensity: | 63.909 |
| Position: | 542.58 | Intensity: | 64.497 |
| Position: | 809.29 | Intensity: | 65.767 |
| Position: | 2669.21 | Intensity: | 65.822 |
| Position: | 445.51 | Intensity: | 66.011 |
| Position: | 845.18 | Intensity: | 66.497 |
| Position: | 948.80 | Intensity: | 66.778 |
| Position: | 833.99 | Intensity: | 66.684 |
| Position: | 609.37 | Intensity: | 67.121 |
| Position: | 2533.76 | Intensity: | 67.213 |
| Position: | 426.44 | Intensity: | 67.276 |
| Position: | 671.03 | Intensity: | 67.978 |
| Position: | 473.19 | Intensity: | 67.902 |
| Position: | 725.03 | Intensity: | 68.787 |
| Position: | 465.32 | Intensity: | 68.975 |
| Position: | 456.91 | Intensity: | 69.207 |
| Position: | 750.53 | Intensity: | 70.083 |

Fig 7 (cont'd)

ID: SPT10203AP1

Comment:

Scan Type: Normal
Start Angle: 5 deg.
Stop Angle: 40 deg.
Num Points: 1751
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | Position (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 9.1912 | 9.6138 | 0.0000 | 0.0000 | 1606.45 | 100.00 | 0.1400 | 0.0000 | 224.9 | PFind | None | 0.00 | 0.00 | None |
| 9.9800 | 8.8557 | 0.0000 | 0.0000 | 1086.27 | 67.62 | 0.0000 | 0.0000 | 130.4 | PFind | None | 0.00 | 0.00 | None |
| 18.8937 | 4.6930 | 0.0000 | 0.0000 | 766.67 | 47.72 | 0.1200 | 0.0000 | 92.0 | PFind | None | 0.00 | 0.00 | None |
| 15.2725 | 5.7967 | 0.0000 | 0.0000 | 733.90 | 45.68 | 0.1400 | 0.0000 | 117.4 | PFind | None | 0.00 | 0.00 | None |
| 16.1681 | 5.4775 | 0.0000 | 0.0000 | 709.22 | 44.15 | 0.1600 | 0.0000 | 113.5 | PFind | None | 0.00 | 0.00 | None |
| 25.7400 | 3.4582 | 0.0000 | 0.0000 | 661.22 | 41.16 | 0.1400 | 0.0000 | 105.8 | PFind | None | 0.00 | 0.00 | None |
| 27.0682 | 3.2917 | 0.0000 | 0.0000 | 539.37 | 33.58 | 0.1200 | 0.0000 | 86.3 | PFind | None | 0.00 | 0.00 | None |
| 27.1100 | 3.2865 | 0.0000 | 0.0000 | 533.27 | 33.20 | 0.0200 | 0.0000 | 85.3 | PFind | None | 0.00 | 0.00 | None |
| 20.8200 | 4.2630 | 0.0000 | 0.0000 | 460.32 | 28.65 | 0.1000 | 0.0000 | 73.7 | PFind | None | 0.00 | 0.00 | None |
| 11.5750 | 7.6387 | 0.0000 | 0.0000 | 412.17 | 25.52 | 0.1600 | 0.0000 | 61.9 | PFind | None | 0.00 | 0.00 | None |
| 18.4781 | 4.7976 | 0.0000 | 0.0000 | 360.05 | 22.41 | 0.1600 | 0.0000 | 57.6 | PFind | None | 0.00 | 0.00 | None |
| 24.5156 | 3.6281 | 0.0000 | 0.0000 | 269.20 | 16.76 | 0.1200 | 0.0000 | 43.1 | PFind | None | 0.00 | 0.00 | None |
| 20.2200 | 4.3881 | 0.0000 | 0.0000 | 263.33 | 16.39 | 0.0400 | 0.0000 | 15.8 | PFind | None | 0.00 | 0.00 | None |
| 24.3000 | 3.6598 | 0.0000 | 0.0000 | 256.67 | 15.98 | 0.0600 | 0.0000 | 20.5 | PFind | None | 0.00 | 0.00 | None |
| 13.0315 | 6.7849 | 0.0000 | 0.0000 | 226.16 | 14.07 | 0.0600 | 0.0000 | 27.1 | PFind | None | 0.00 | 0.00 | None |
| 26.0700 | 3.4152 | 0.0000 | 0.0000 | 210.00 | 13.07 | 0.1200 | 0.0000 | 21.0 | PFind | None | 0.00 | 0.00 | None |
| 23.0362 | 3.8576 | 0.0000 | 0.0000 | 205.88 | 12.82 | 0.0800 | 0.0000 | 24.7 | PFind | None | 0.00 | 0.00 | None |
| 26.2200 | 3.3960 | 0.0000 | 0.0000 | 201.67 | 12.55 | 0.0600 | 0.0000 | 4.0 | PFind | None | 0.00 | 0.00 | None |
| 14.1331 | 6.2613 | 0.0000 | 0.0000 | 195.68 | 12.18 | 0.1600 | 0.0000 | 19.6 | PFind | None | 0.00 | 0.00 | None |
| 29.0200 | 3.0744 | 0.0000 | 0.0000 | 180.00 | 11.20 | 0.1600 | 0.0000 | 14.4 | PFind | None | 0.00 | 0.00 | None |
| 28.2644 | 3.1548 | 0.0000 | 0.0000 | 168.65 | 10.50 | 0.0600 | 0.0000 | 20.2 | PFind | None | 0.00 | 0.00 | None |
| 11.9200 | 7.4184 | 0.0000 | 0.0000 | 168.33 | 10.48 | 0.0600 | 0.0000 | 26.9 | PFind | None | 0.00 | 0.00 | None |
| 24.9800 | 3.5617 | 0.0000 | 0.0000 | 166.67 | 10.37 | 0.1600 | 0.0000 | 10.0 | PFind | None | 0.00 | 0.00 | None |
| 12.1800 | 7.2606 | 0.0000 | 0.0000 | 161.70 | 10.07 | 0.1000 | 0.0000 | 22.6 | PFind | None | 0.00 | 0.00 | None |
| 28.1506 | 3.1673 | 0.0000 | 0.0000 | 157.65 | 9.81 | 0.0200 | 0.0000 | 22.1 | PFind | None | 0.00 | 0.00 | None |
| 19.2400 | 4.6093 | 0.0000 | 0.0000 | 153.33 | 9.54 | 0.1600 | 0.0000 | 6.1 | PFind | None | 0.00 | 0.00 | None |
| 24.9000 | 3.5729 | 0.0000 | 0.0000 | 146.67 | 9.13 | 0.1600 | 0.0000 | 23.5 | PFind | None | 0.00 | 0.00 | None |
| 23.4091 | 3.7972 | 0.0000 | 0.0000 | 141.87 | 8.83 | 0.1400 | 0.0000 | 8.5 | PFind | None | 0.00 | 0.00 | None |
| 13.3200 | 6.6417 | 0.0000 | 0.0000 | 135.00 | 8.40 | 0.0200 | 0.0000 | 2.7 | PFind | None | 0.00 | 0.00 | None |
| 30.9037 | 2.8911 | 0.0000 | 0.0000 | 123.85 | 7.71 | 0.0200 | 0.0000 | 7.4 | PFind | None | 0.00 | 0.00 | None |
| 28.8937 | 3.0875 | 0.0000 | 0.0000 | 121.18 | 7.54 | 0.1200 | 0.0000 | 14.5 | PFind | None | 0.00 | 0.00 | None |
| 9.4200 | 9.3808 | 0.0000 | 0.0000 | 120.00 | 7.47 | 0.0800 | 0.0000 | 0.0 | PFind | None | 0.00 | 0.00 | None |
| 28.4600 | 3.1336 | 0.0000 | 0.0000 | 106.67 | 6.64 | 0.0600 | 0.0000 | 2.1 | PFind | None | 0.00 | 0.00 | None |
| 31.0800 | 2.8751 | 0.0000 | 0.0000 | 105.00 | 6.54 | 0.0000 | 0.0000 | 0.0 | PFind | None | 0.00 | 0.00 | None |

FIG. 8 (cont'd)

| | | | |
|---|---|---|---|
| Position: | 1258.84 | Intensity: | 33.820 |
| Position: | 1606.84 | Intensity: | 35.302 |
| Position: | 1034.40 | Intensity: | 37.929 |
| Position: | 2455.38 | Intensity: | 39.481 |
| Position: | 1280.32 | Intensity: | 40.410 |
| Position: | 471.14 | Intensity: | 40.065 |
| Position: | 1121.83 | Intensity: | 40.697 |
| Position: | 2937.03 | Intensity: | 40.872 |
| Position: | 1055.21 | Intensity: | 41.636 |
| Position: | 428.03 | Intensity: | 41.741 |
| Position: | 3483.36 | Intensity: | 42.231 |
| Position: | 832.09 | Intensity: | 43.113 |
| Position: | 434.84 | Intensity: | 42.999 |
| Position: | 440.64 | Intensity: | 43.870 |
| Position: | 458.30 | Intensity: | 44.097 |
| Position: | 1334.26 | Intensity: | 44.865 |
| Position: | 414.04 | Intensity: | 44.657 |
| Position: | 1510.61 | Intensity: | 45.504 |
| Position: | 484.32 | Intensity: | 45.538 |
| Position: | 811.23 | Intensity: | 45.676 |
| Position: | 2611.72 | Intensity: | 47.063 |
| Position: | 449.24 | Intensity: | 47.115 |
| Position: | 620.34 | Intensity: | 47.594 |
| Position: | 558.39 | Intensity: | 47.940 |
| Position: | 420.16 | Intensity: | 48.158 |
| Position: | 576.49 | Intensity: | 48.689 |
| Position: | 668.31 | Intensity: | 48.925 |
| Position: | 747.48 | Intensity: | 48.960 |
| Position: | 507.29 | Intensity: | 49.247 |
| Position: | 953.27 | Intensity: | 49.389 |
| Position: | 725.20 | Intensity: | 50.152 |
| Position: | 873.83 | Intensity: | 51.143 |
| Position: | 405.47 | Intensity: | 51.684 |
| Position: | 783.53 | Intensity: | 53.794 |

CRYSTAL FORMS OF IRINOTECAN HYDROCHLORIDE

RELATED APPLICATIONS

This application claims priority from U.S. Provisional Patent Application Ser. No. 60/718,827 which was filed on Sep. 20, 2005. The entire content of U.S. Provisional Patent Application Ser. No. 60/718,827 is incorporated herein as reference.

BACKGROUND OF THE INVENTION

1. Field of the Invention

The present invention relates to 7-ethyl-10-[4-(1-piperidino)-1-piperidino]carbonyloxycamptothecin monohydrochloride trihydrate (irinotecan hydrochloride). More particularly, it relates to newly discovered crystalline forms having increased ease of filtering over previously produced irinotecan hydrochloride, to processes for producing these new crystalline forms, to pharmaceutical compositions containing the new forms, and methods of treating metastatic carcinoma of the colon or rectum using these new forms 2. Description of the Related Art 7-ethyl-10-[4-(1-piperidino)-1-piperidino]carbonyloxycamptothecin monohydrochloride trihydrate having the molecular structure:

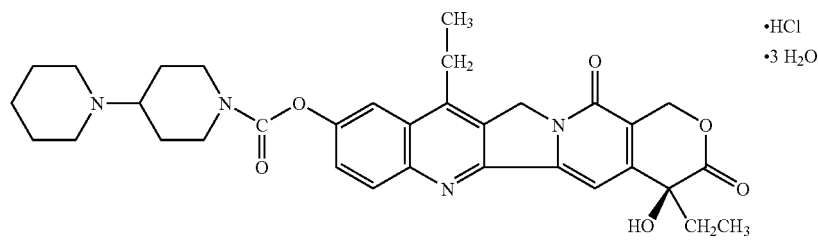

Irinotecan Hydrochloride and formula $C_{33}H_{38}N_4O_6 \cdot HCl \cdot 3H_2O$ and a molecular weight of 677.19 is an antineoplastic agent of the topoisomerase I inhibitor class. Irinotecan hydrochloride is a semisynthetic derivative of camptothecin, and alkaloid extract from plants such as *Camptotheca acuminata*. Irinotecan hydrochloride is approved by the Food and Drug Administration as a component of first-line therapy in combination with 5-fluorouracil and leucovorin for patients with metastatic carcinoma of the colon or rectum. It is also approved for treating patients with metastatic carcinoma of the colon or rectum whose disease has recurred or progressed following initial fluorouracil-based therapy. *Physicians' Desk Reference*, 59th ed., 2005. Irinotecan hydrochloride is commercially available in injection form under the trade name Camptosar®.

The present invention relates to novel solid state crystalline forms of irinotecan hydrochloride.

U.S. Pat. No. 4,604,463 discloses various processes for preparing global irinotecan and irinotecan hydrochloride. The '463 patent is incorporated by reference in its entirety and, specifically, for its teachings regarding the synthesis of irinotecan and irinotecan hydrochloride from commercially available and readily accessible starting materials.

In Example 19 of the '463 patent, 7-ethyl-10-[4-(1-piperidino)-1-piperidino]carbonyloxycamptothecin was formed by suspending 10-Chlorocarbonyloxy-7-ethylcamptothecin in dry dioxane. 4-piperidinopiperidine was added to this suspension. The mixture was stirred until the starting materials were consumed. The solvent was then removed by distillation under reduced pressure and the residue was subjected to separation and purification by the aid of column chromatography on silica gel whereby 7-ethyl-10-[4(1-piperidino)-1-piperidino]carbonyloxycamptothecin was obtained.

In Example 28 of the '463 patent, 7-ethyl-10-[4-(1-piperidino)-1-piperidino]carbonyloxycamptothecin was formed by dissolving 7-ethyl-10-hydroxycamptothecin and 1-chlorocarbonyl-4-piperidinopiperidine in anhydrous pyridine, and the mixture was stirred for 1 hour at room temperature. The reaction mixture was evaporated to dryness in vacuo and the residue was dissolved in $CHCl_3$. The solution was washed successively with a 7% aqueous solution of $NaHCO_3$, a saturated aqueous solution NaCl, and the $CHCl_3$ layer was dried with $MgSO_4$, filtered, and evaporated in vacuo. The residual material was decolorized by passing it through a short silica gel column whereby 7-ethyl-10-[4(1-piperidino)-1piperidino]carbonyloxycamptothecin was obtained as a pale yellow mass, which was recrystallized from ethanol to give colorless needles.

In Example 37 of the '463 patent, 7-ethyl-10-[4-(1-piperidino)-1-piperidino]carbonyloxycamptothecin hydrochloride was formed by adding 1/10N HCl to an ice-cooled suspension of 7-ethyl-10-[1-(4-piperidino)piperidino]carbonyloxycamptothecin in distilled water. The suspension was stirred vigorously for 5 minutes under cooling in an ice bath. The solution was passed through a filter (0.22 µm, SLGS 025 OS) and the filtrate was lyophilized overnight whereby 7-ethyl-10-[4-(1-piperidino)-1-piperidino]carbonyloxycamptothecin hydrochloride was obtained as a pale yellow amorphous solid.

We have now discovered and characterized novel crystalline forms of irinotecan hydrochloride that are more easily handled during the manufacturing process than previously known forms of irinotecan hydrochloride.

There is a need for new crystalline forms of irinotecan hydrochloride. The discovery of new crystalline forms of a pharmaceutical compound provides an improved manner of processing and producing a pharmaceutical product containing irinotecan hydrochloride. New crystalline forms increase the possibilities available to a scientist involved in the formulation of pharmaceutical products thereby allowing for the formulation of new and improved pharmaceutical compositions that would otherwise be unattainable, but for the invention of the new crystalline forms.

SUMMARY OF THE INVENTION

A first aspect of the present invention is directed to crystalline Form I of irinotecan hydrochloride. Form I is identifiable by its X-ray diffraction pattern. Irinotecan hydrochloride Form I can be prepared under controlled conditions using solvents of ethanol, N-heptane, and hydrochloric acid.

A second aspect of the present invention is directed to crystalline Form II of irinotecan hydrochloride. Form II is identifiable by its X-ray diffraction pattern. Irinotecan hydrochloride Form II can be prepared under controlled conditions using solvents of ethanol and hydrochloric acid.

A third aspect of the present invention is directed to crystalline Form III of irinotecan hydrochloride. Form III is identifiable by its X-ray diffraction pattern. Irinotecan hydrochloride Form III can be prepared under controlled conditions using solvents of methanol, ethyl acetate, and hydrochloric acid.

A fourth aspect of the present invention is directed to crystalline Form IV of irinotecan hydrochloride. Form IV is identifiable by its X-ray diffraction pattern. Irinotecan hydrochloride Form IV can be prepared under controlled conditions using solvents of ethanol, ethyl acetate, and hydrochloric acid.

The present invention provides crystalline forms of irinotecan hydrochloride that are more easily filtered from solution over the existing form of irinotecan hydrochloride. This increased ease of filtering is useful because it allows for ease in handling and processing the irinotecan hydrochloride during the manufacturing process.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

In a first aspect, the present invention provides a new crystalline form of irinotecan hydrochloride with increased ease of filtering, designated Form I. Form I has been characterized by powder X-ray diffraction ("PXRD") analysis and infrared diffuse reflectance analysis. The PXRD and infrared diffuse reflectance patterns are provided as figures (FIGS. 1 and 2, respectively).

Figure 1:
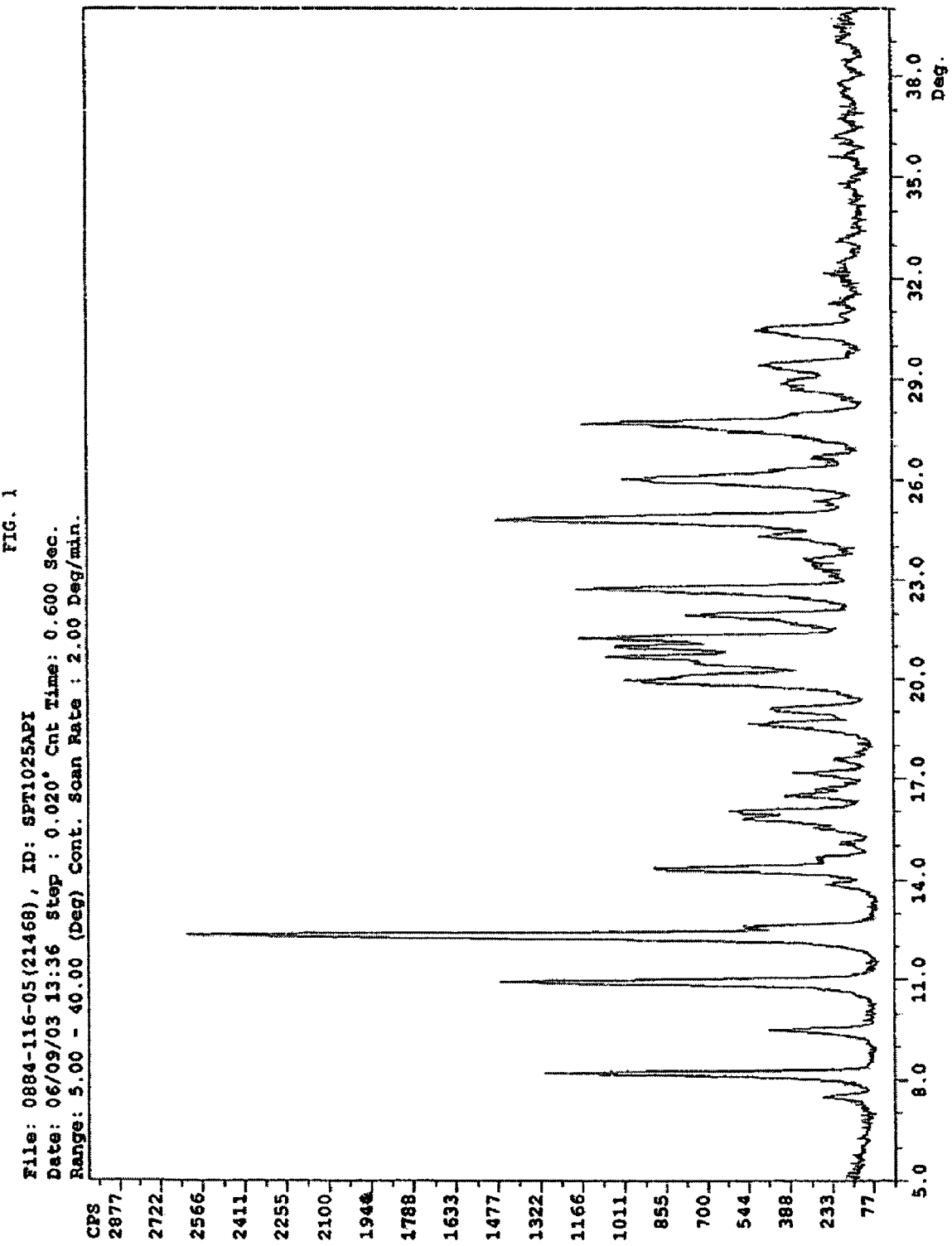
FIG. 1 is a characteristic powder X-ray diffraction pattern of Form I.
Figure 2:
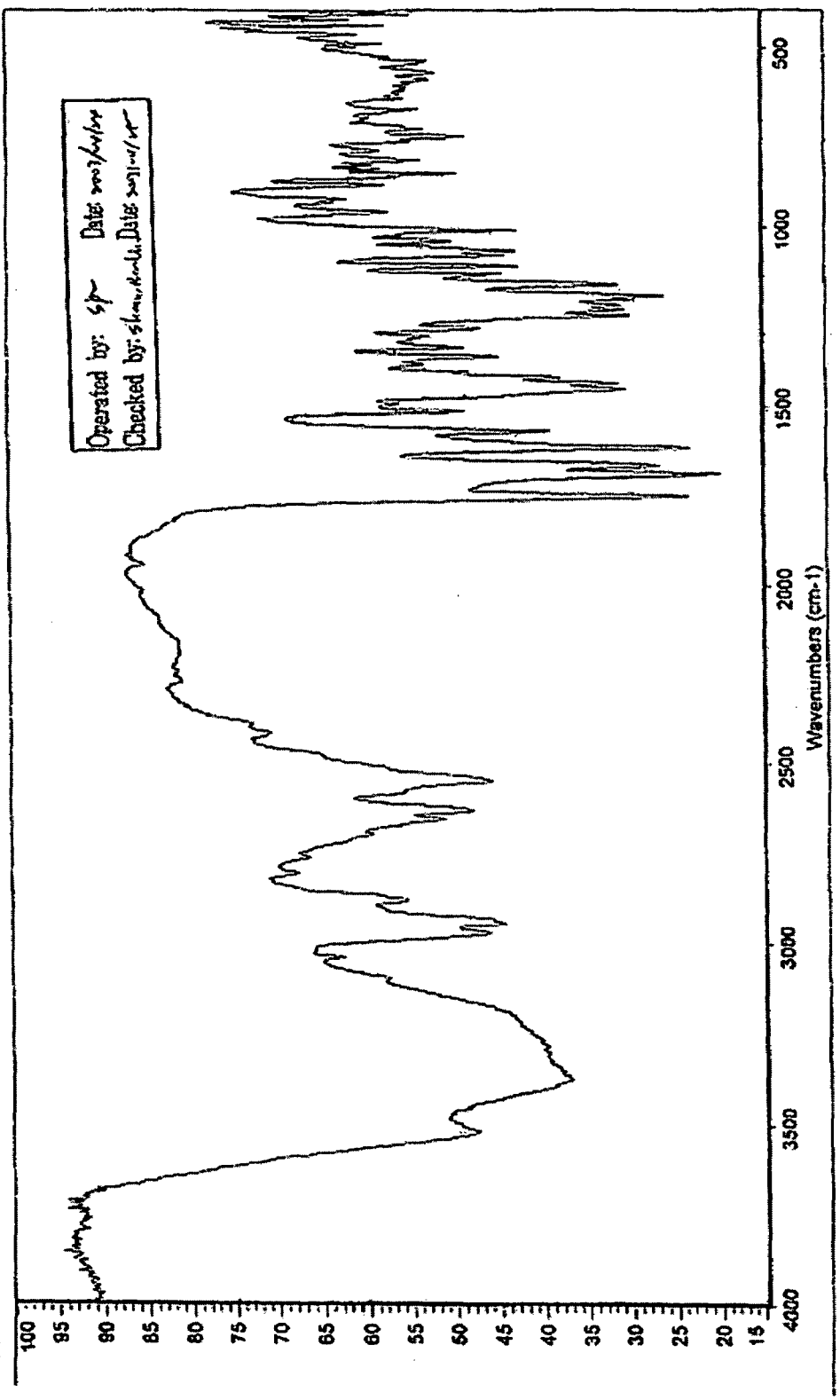
FIG. 2 is an infrared diffuse reflectance pattern of Form I.
Figure 2:
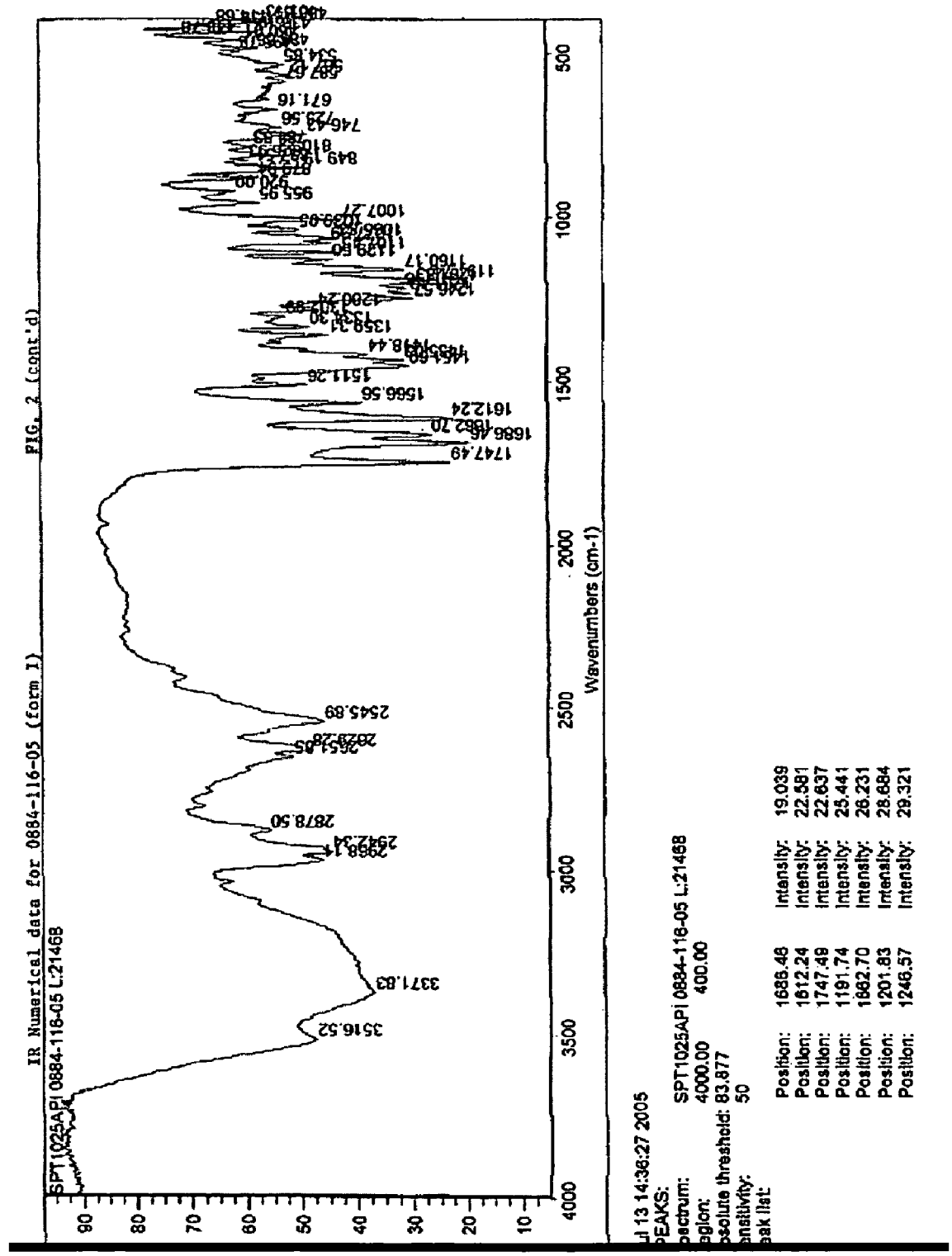

Referring to FIG. 1, the PXRD of irinotecan hydrochloride Form I is unique. Form I may be characterized by the PXRD characteristics set forth in Table 1 which distinguishes it from Forms II, III, and IV.

The test sample was milled and homogenously put on the tray of the X-ray machine, Scintag $X_2$Advance Diffraction, tested at continuous scan rate of 2.00 Deg/min, with range 5.00-40.00(Deg.) and at a wavelength of 1.540562.

TABLE 1

| Peak Position (two theta) | Intensity (cps) |
| --- | --- |
| 12.3406 | 1662.63 |
| 24.7913 | 913.23 |
| 10.9438 | 891.13 |
| 8.2056 | 762.43 |
| 27.6750 | 663.63 |
| 22.7206 | 648.02 |
| 21.2350 | 619.23 |

Referring to FIG. 2, the infrared diffuse reflectance pattern of irinotecan hydrochloride Form I demonstrates the unique characteristic of Form I.

We weighed about 3 mg of sample and disperse the sample homogenously in 300 mg dry KBr, and then, immediately record the spectrum between 400 to 4000 $cm^{-1}$ by diffuse reflectance. We performed a single test on each sample. The IR machine is Nicolet, Magna-IR 560 Spectrometer. The number of sample scans is 32. The number of background scans is 32. The resolution is 4. The sample gain is 8. The mirror velocity is 0.6329. The aperture is 100.

The loss on drying (LOD) of Form I was determined to be 7.9 %. The LOD was tested using TA instrument 2950.

Irinotecan hydrochloride Form I has been prepared under conditions described in Example 1. Other conditions under which irinotecan hydrochloride Form I is produced may be found by routine experimentation.

Irinotecan hydrochloride Form I may be prepared by crystallizing irinotecan hydrochloride from a solution of ethanol, hydrochloric acid, and N-heptane.

In its second aspect, the present invention provides another new crystalline form of irinotecan hydrochloride with increased ease of filtering, designated Form II. Form II has been characterized by PXRD analysis and infrared diffuse reflectance analysis. The PXRD and infrared diffuse reflectance patterns are provided as figures (FIGS. 3 and 4, respectively).

Figure 3:
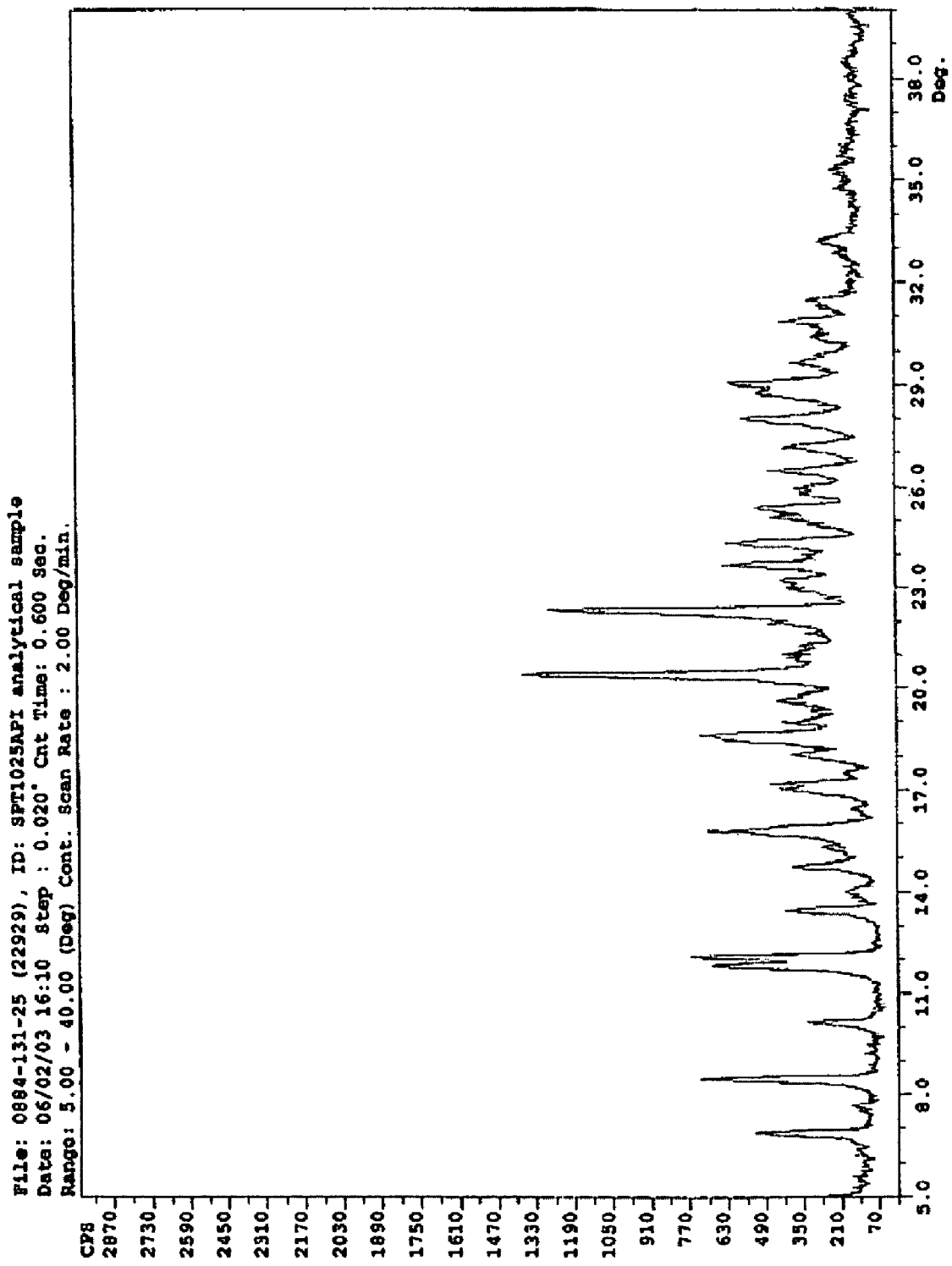
FIG. 3 is a characteristic powder X-ray diffraction pattern of Form II.
Figure 4:
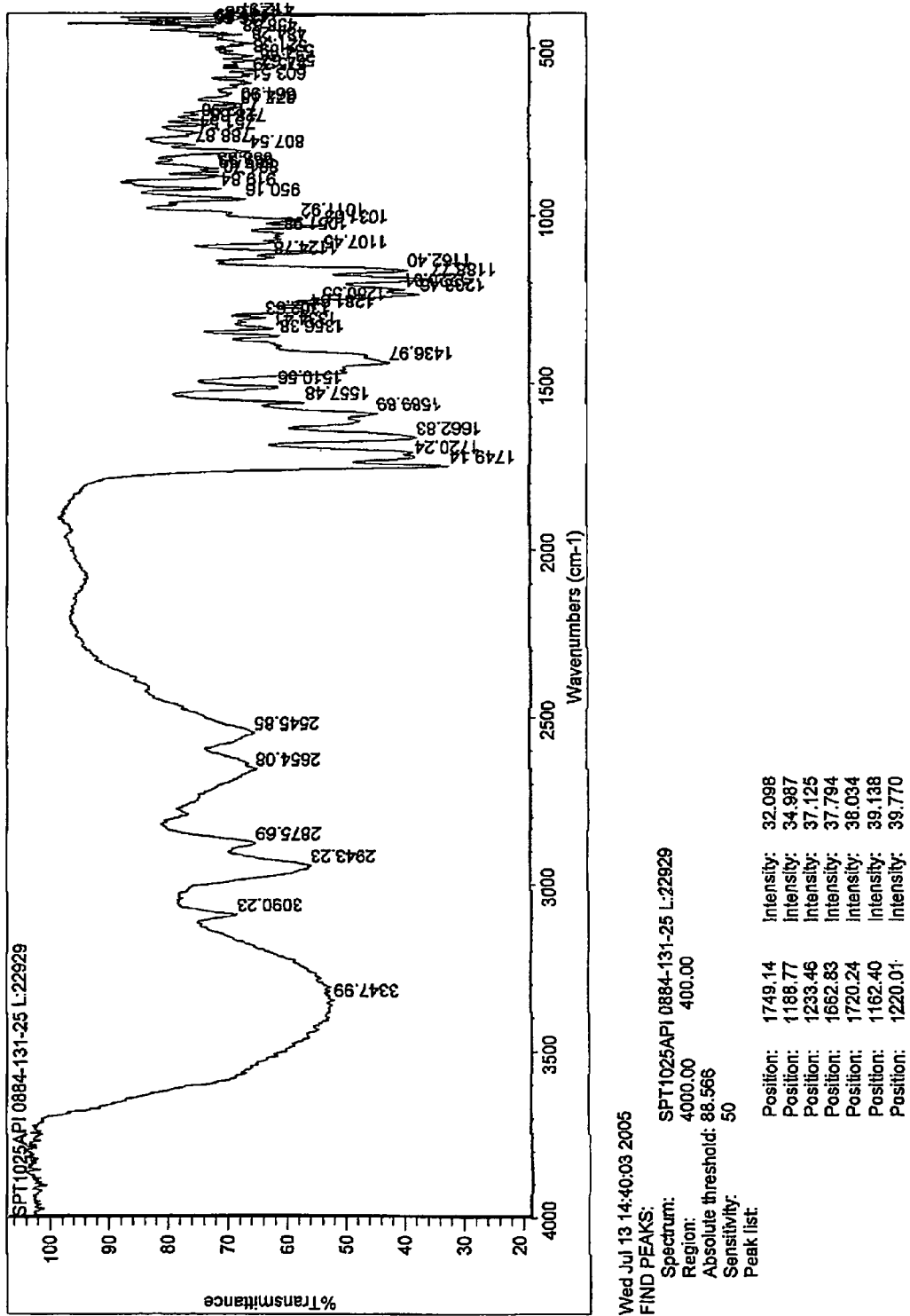
FIG. 4 is an infrared diffuse reflectance pattern of Form II.

Referring to FIG. 3, the PXRD of irinotecan hydrochloride Form II is unique. Form 11 may be characterized by the PXRD characteristics set forth in Table 2 which distinguish it from Forms I, III, and IV.

The PXRD of FIG. 3 was performed using identical equipment and sample preparations as were used to characterize Form I. Further, the testing procedures used to determine PXRD, loss on drying and infrared diffuse reflectance are the same for all the crystalline forms of irinotecan hydrochloride of the present invention.

TABLE 2

| Peak Position (two theta) | Intensity (cps) |
| --- | --- |
| 20.3956 | 746.23 |
| 22.2950 | 719.65 |

TABLE 2-continued

| Peak Position (two theta) | Intensity (cps) |
| --- | --- |
| 12.0744 | 428.83 |
| 8.4800 | 396.32 |
| 11.8306 | 381.37 |
| 15.7587 | 319.98 |
| 18.5200 | 301.87 |

Referring to FIG. 4, the infrared diffuse reflectance pattern of irinotecan hydrochloride Form II demonstrates the unique characteristic of Form II.

The infrared diffuse reflectance of FIG. 4 was performed using identical equipment and sample preparations as were used to characterize Form I.

The loss on drying of Form I was determined to be 7.8 %.

Irinotecan hydrochloride Form II has been prepared under conditions described in Example 2. Other conditions under which irinotecan hydrochloride Form II is produced may be found by routine experimentation.

Irinotecan hydrochloride Form II may be prepared by crystallizing irinotecan hydrochloride from a solution of ethanol and hydrochloric acid.

In its third aspect, the present invention provides another new crystalline form of irinotecan hydrochloride having increased ease of filtering, designated Form III. Form III has been characterized by powder X-ray diffraction ("PXRD") analysis and infrared diffuse reflectance analysis. The PXRD and infrared diffuse reflectance patterns are provided as figures (FIGS. 5 and 6, respectively).

Figure 5:
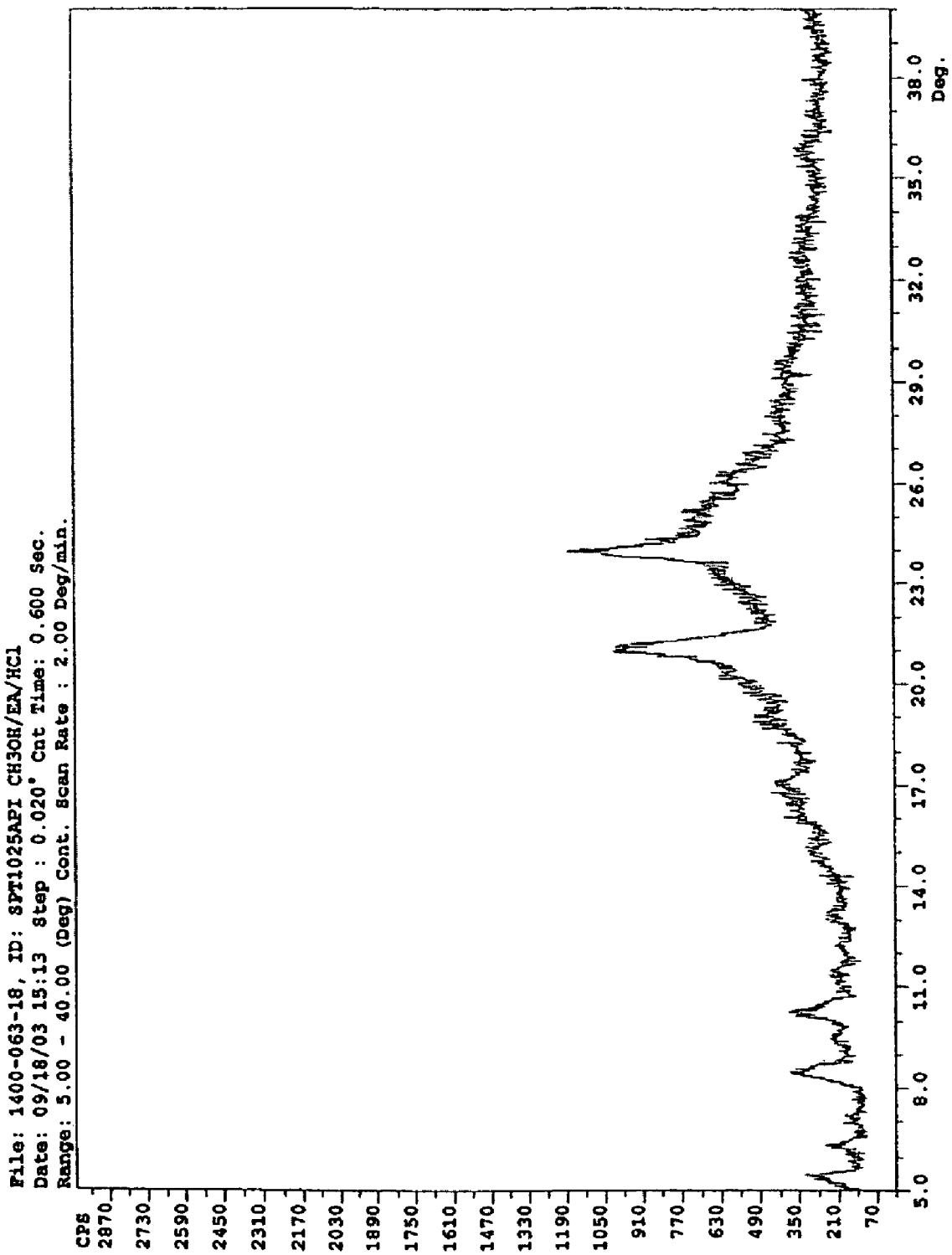
FIG. 5 is a characteristic powder X-ray diffraction pattern of Form III.
Figure 6:
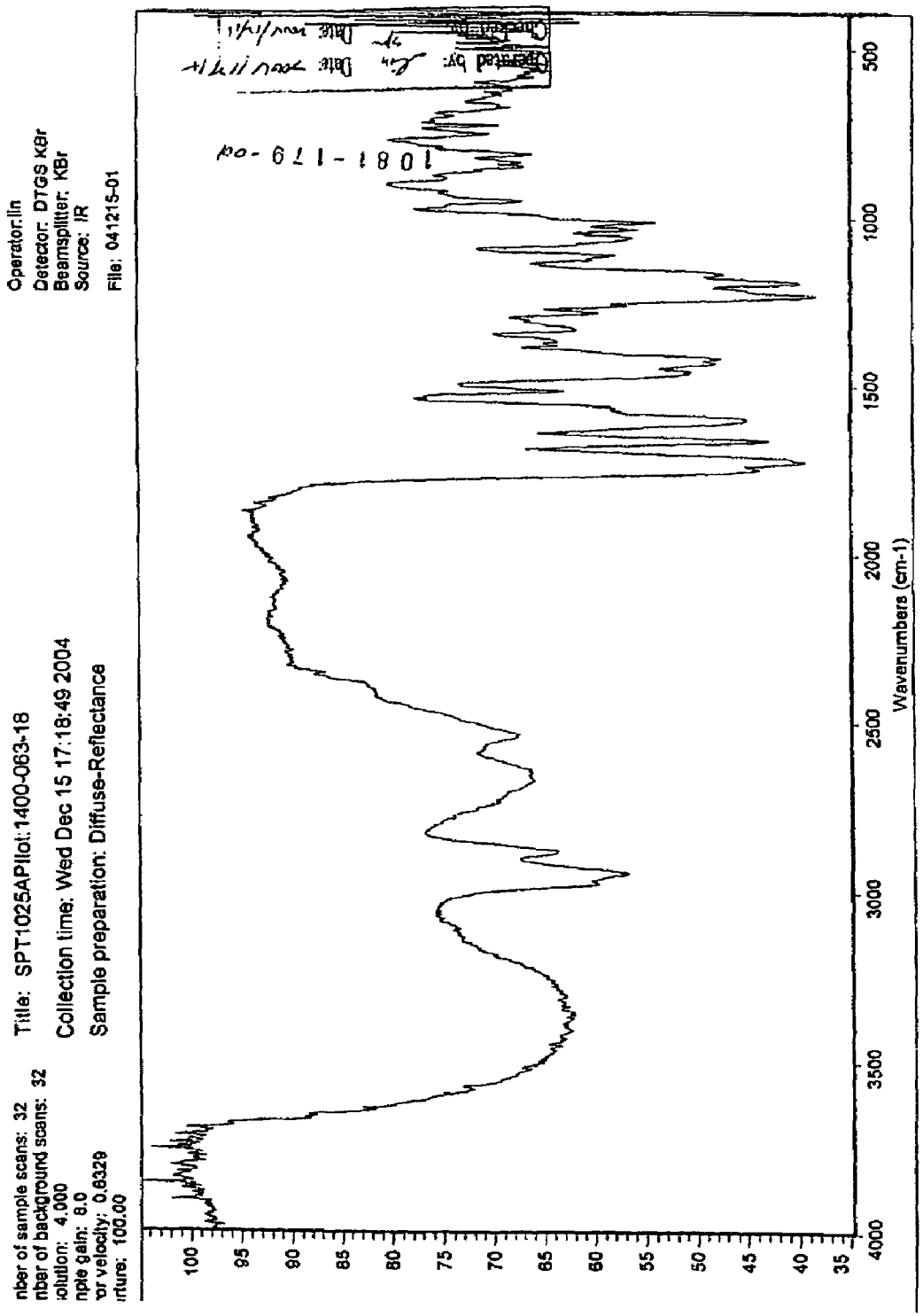
FIG. 6 is an infrared diffuse reflectance pattern of Form III.
Figure 6:
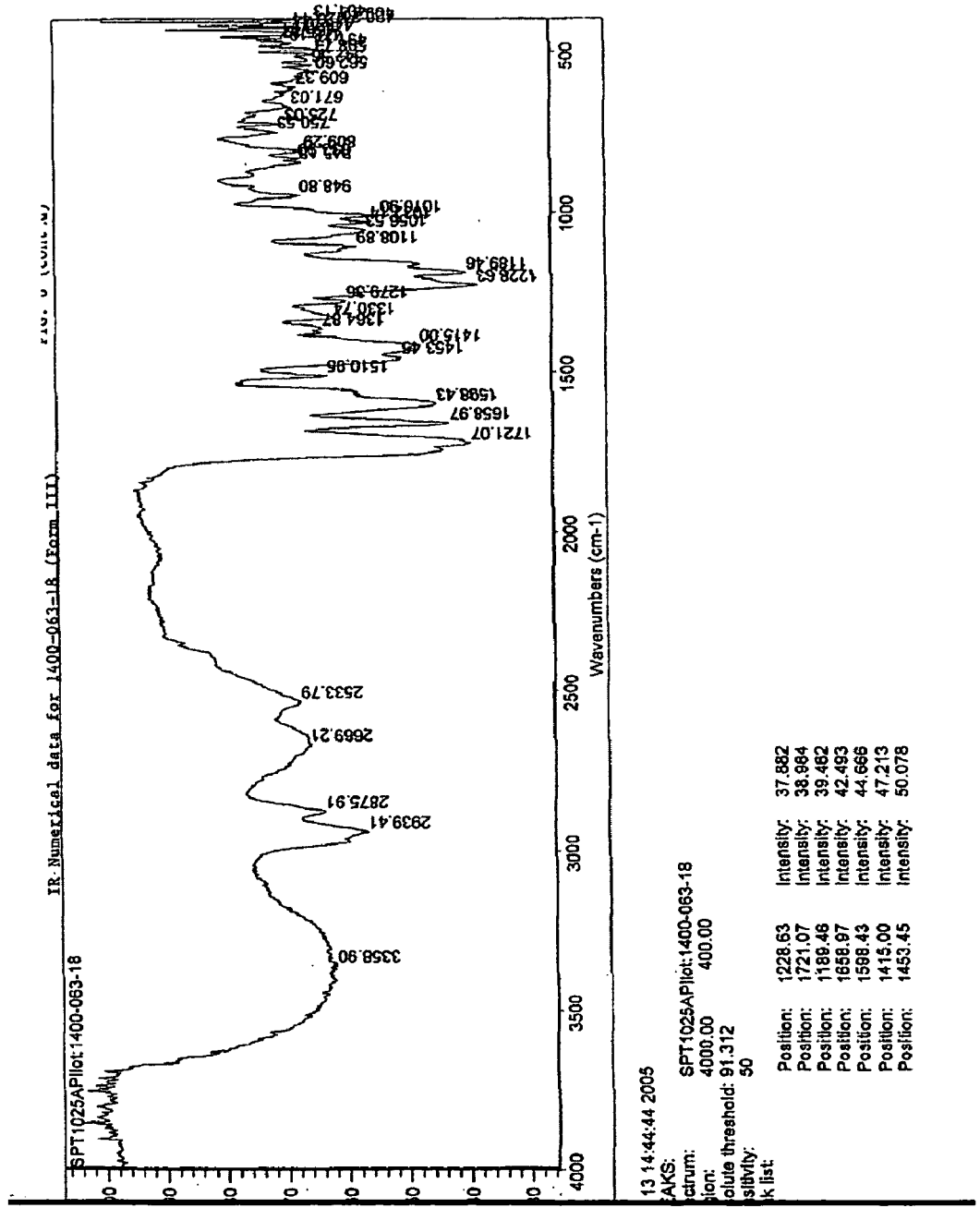

Referring to FIG. 5, the PXRD of irinotecan hydrochloride Form III is unique. Form III may be characterized by the PXRD characteristics set forth in Table 3 which distinguish it from Forms I, II, and IV.

The PXRD of FIG. 5 was performed using identical equipment and sample preparations as were used to characterize Forms I and II.

TABLE 3

| Peak Position (two theta) | Intensity (cps) |
| --- | --- |
| 23.9600 | 421.67 |
| 20.9200 | 365.00 |
| 21.0800 | 331.67 |
| 21.0944 | 308.53 |
| 23.8375 | 295.17 |
| 24.3200 | 236.67 |
| 10.2800 | 153.33 |

Referring to FIG. 6, the infrared diffuse reflectance pattern of irinotecan hydrochloride Form III demonstrates the unique characteristic of Form III.

The infrared diffuse reflectance pattern of FIG. 6 was performed using identical equipment and sample preparations as were used to characterize Forms I and II.

Irinotecan hydrochloride Form III has been prepared under conditions described in Example 3 Other conditions under which irinotecan hydrochloride Form III is produced may be found by routine experimentation.

Irinotecan hydrochloride Form III may be prepared by crystallizing irinotecan hydrochloride from a solution of methanol, ethyl acetate, and hydrochloric acid.

In its fourth aspect, the present invention provides a new crystalline form of irinotecan hydrochloride with increased ease of filtering, designated Form IV. Form IV has been characterized by powder X-ray diffraction ("PXRD") analysis and infrared diffuse reflectance analysis. The PXRD and infrared diffuse reflectance patterns are provided as figures (FIGS. 7 and 8, respectively).

Figure 7:
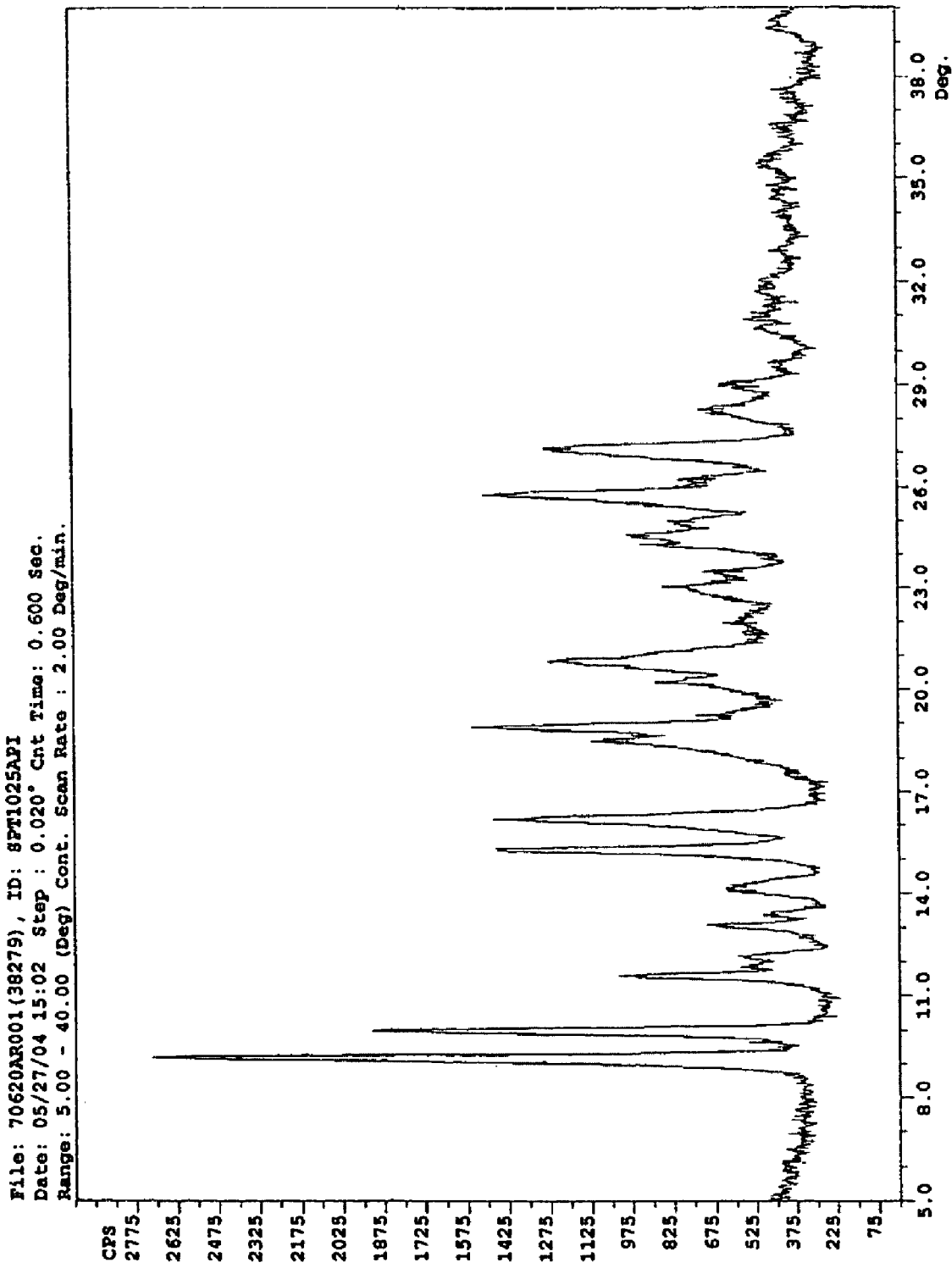
FIG. 7 is a characteristic powder X-ray diffraction pattern of Form IV.
Figure 8:
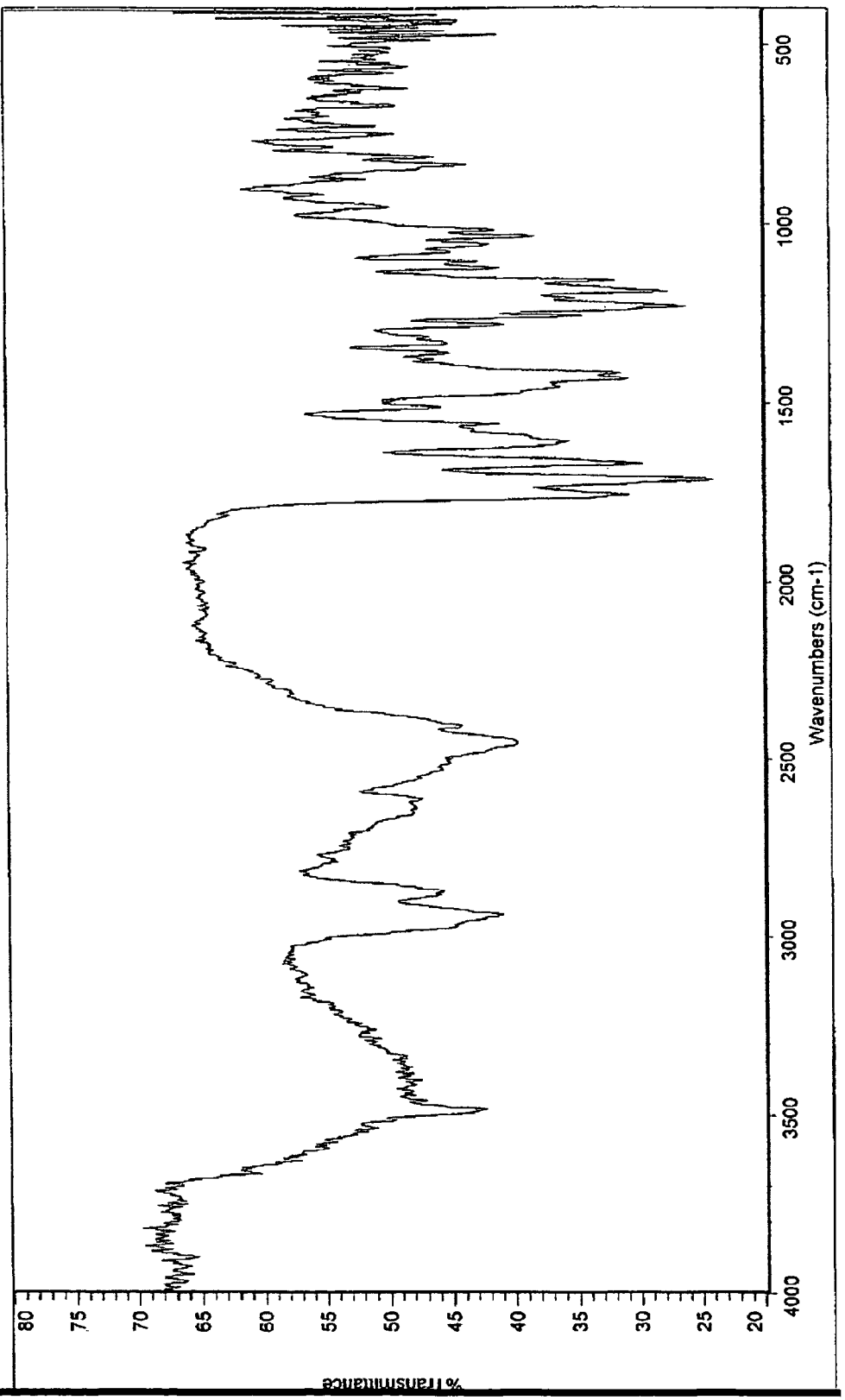
FIG. 8 is an infrared diffuse reflectance pattern of Form IV.
Figure 8:
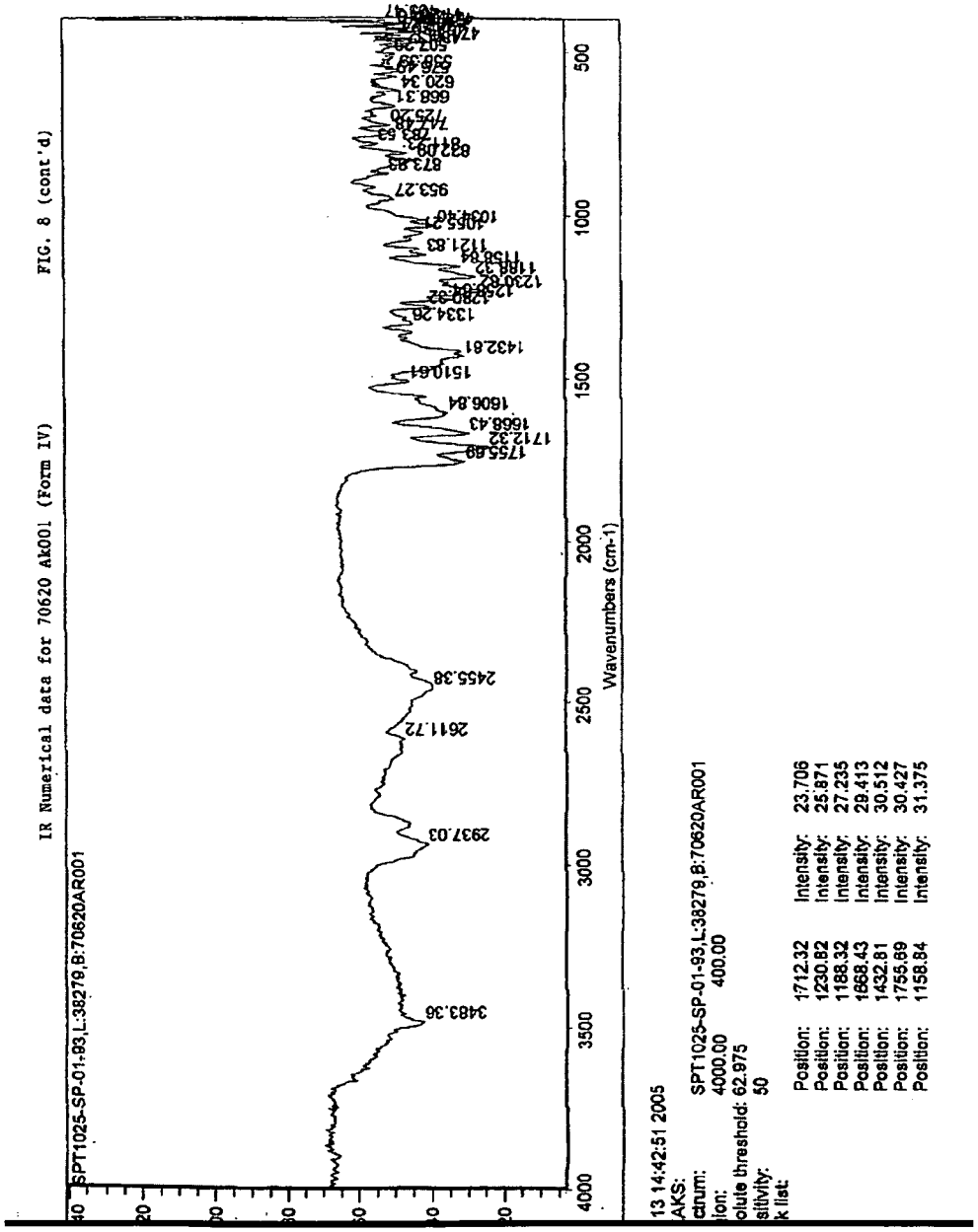
Figure 9:
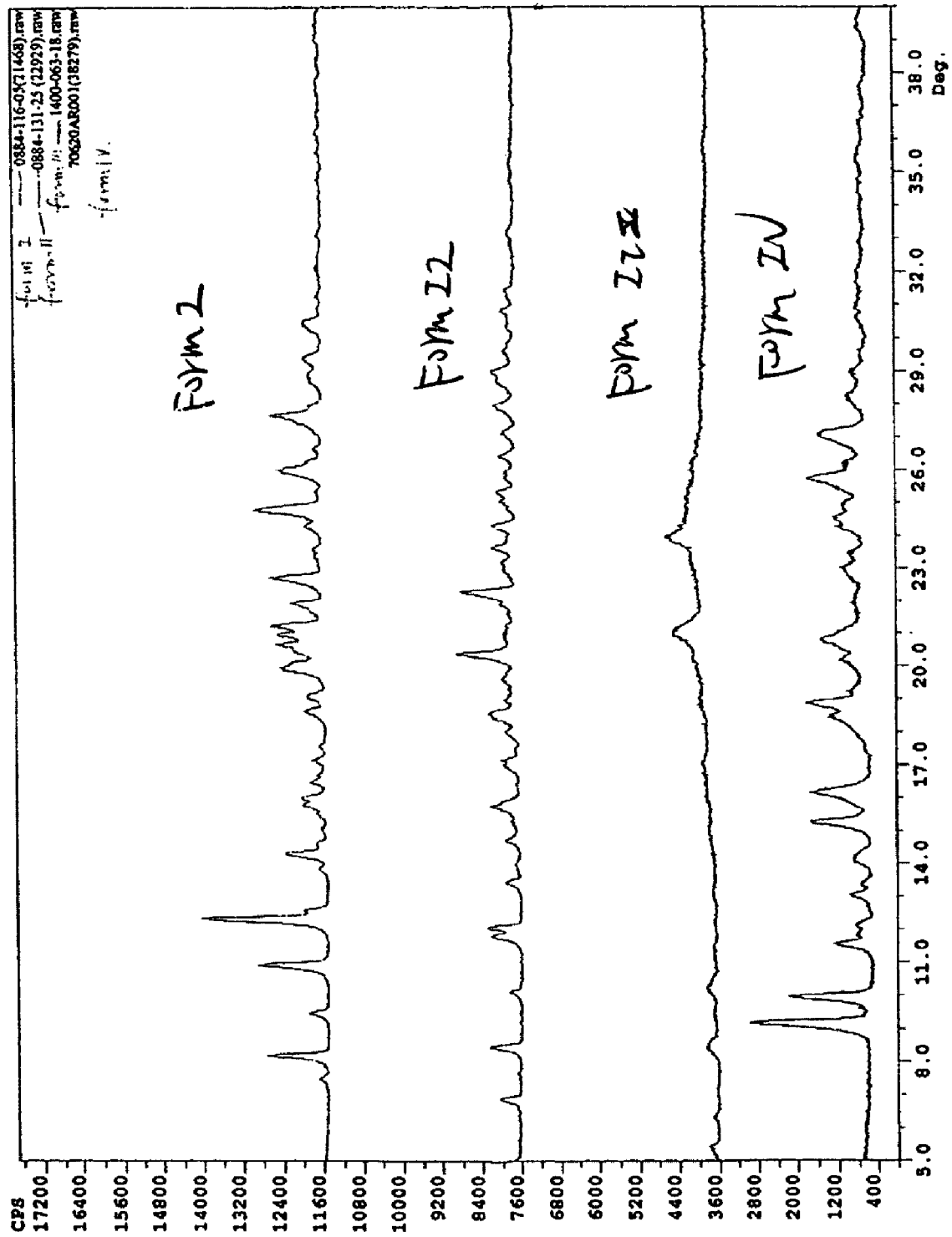
FIG. 9 is a side-by-side comparison of the X-ray diffraction patterns of Forms I to IV.

Referring to FIG. 7, the PXRD of irinotecan hydrochloride Form IV is unique. Form IV may be characterized by the PXRD characteristics set forth in Table 4 which distinguish it from Forms I, II, and III.

The PXRD of FIG. 7 was performed using identical equipment and sample preparations as were used to characterize Forms I, II, and III.

TABLE 4

| Peak Position (two theta) | Intensity (cps) |
| --- | --- |
| 9.1912 | 1606.45 |
| 9.9800 | 1086.27 |
| 18.8937 | 766.67 |
| 15.2725 | 733.90 |
| 16.1681 | 709.22 |
| 25.7400 | 661.22 |
| 27.0662 | 539.37 |

Referring to FIG. 8, the infrared diffuse reflectance pattern of irinotecan hydrochloride Form IV demonstrates the unique characteristic of Form IV.

The infrared diffuse reflectance pattern of FIG. 8 was performed using identical equipment and sample preparations as were used to characterize Forms I, II, and III.

Irinotecan hydrochloride Form IV has been prepared under conditions described in Example 4. Other conditions under which irinotecan hydrochloride Form IV is produced may be found by routine experimentation.

Irinotecan hydrochloride Form IV may be prepared by crystallizing irinotecan hydrochloride from a solution of ethanol, ethyl acetate, and hydrochloric acid.

Irinotecan hydrochloride Forms I, II, III, and IV have utility as the active agent in pharmaceutical compositions and dosage forms for treatment of metastatic carcinoma of the colon or rectum. Irinotecan hydrochloride Forms I, II, III, and IV are also useful for preparing salts and solvates of irinotecan, such as the irinotecan hydrochloride injection that is currently administered to patients in the United States. To the extent that the atomic positions and molecular conformation of irinotecan hydrochloride do not significantly change with salt formation or solvation, such salts and solvates are considered to fall within the scope of the invention.

Irinotecan hydrochloride Forms I, II, III, and IV may be incorporated into pharmaceutical products for administration to a human or other mammal in need of treatment of metastatic carcinoma of the colon or rectum. Pharmaceutical compositions and dosage forms may be formulated for transdermal delivery.

The pharmaceutical composition for transdermal delivery contains such excipients as sorbitol NF powder and lactic acid. The pH of the solution can be adjusted to 3.5 (range 3.0 to 3.8) using sodium hydroxide or hydrochloric acid. This composition is intended to be diluted with 5% Dextrose Injection, USP (D5W), or 0.9% Sodium Chloride Injection, USP, prior to intravenous infusion. The preferred diluent is 5% Dextrose Injection, USP.

Pharmaceutical compositions and dosage forms of this invention can be administered to a patient for the purpose of treating metastatic carcinoma of the colon or rectum in the manner that compositions containing known irinotecan hydrochloride have been administered. For this purpose, irinotecan hydrochloride Form I, II, III, and/or IV is administered preferably in an amount of from about 75 to 180 mg/m$^2$.

Having thus described the invention with respect to certain preferred embodiments, the invention will now be further illustrated with the following non-limiting examples.

EXAMPLES

Preparation of Irinotecan Hydrochloride Form I

Example 1

To a suitable vessel were charged amorphous irinotecan acetate (6.35 g) and ethanol (45 mL). The resulting mixture was heated to reflux (about 70° C.) and remained as a suspension. 2N HCl (5.4 mL) was added to the reaction mixture to adjust the pH to less than 4. N-heptane (25 mL) and ethanol (30 mL) were added to the resulting mixture. The solution was then cooled to 0~10° C. and stirred at this temperature for 1 hour, and then charged with 200 mL of ethyl acetate in order to perform a solvent swap. The solution was then filtrated and washed with ethyl acetate (50 mL). The solid was dried in vacuum. Due to a lower than expected water content, the solid was heated under high humidity for one hour and then cooled to give irinotecan hydrochloride trihydrate Form I (6.6 g).

Preparation of Irinotecan Hydrochloride Form II

Example 2

To a suitable vessel were charged amorphous irinotecan acetate (14.5 g) and ethanol (101 mL). The resulting mixture was heated to reflux and remained as a suspension. 2N HCl (10 mL) was added to the reaction mixture to adjust the pH to less than 4. Ethyl Acetate (145 mL) was added to the resulting mixture. The mixture was then cooled to 0~10° C. and stirred at this temperature for 1 hour, filtrated, and washed with ethyl acetate (100 mL). The solid was then dried in vacuum. Due to a lower than expected water content, the solid was put under atmosphere overnight to give irinotecan hydrochloride trihydrate Form II (13.5 g).

Preparation of Irinotecan Hydrochloride Form III

Example 3

To a 100 mL reactor was charged amorphous irinotecan acetate (2.0 g) and methanol (14 mL). The reaction mixture was heated to 50° C. 2N hydrochloric acid (6.2 wt %, about 1.7 mL) was added to adjust the pH level to less than 4 in order to dissolve the solid particles. Ethyl acetate (40 mL) was added slowly to the mixture. The mixture was cooled to 0~10° C. and stirred at this temperature for 1 hour. The solid particles were filtered and washed with cooled ethyl acetate (6 mL). The wet cake was dried in vacuum to give 1.66 g of irinotecan hydrochloride trihydrate Form III.

Preparation of Irinotecan Hydrochloride Form IV

Example 4

To a 16 L reactor was charged amorphous irinotecan acetate (234 g) and ethanol (1300 g). The reaction mixture was heated to reflux. 9N Hydrochloric acid (14.3 wt %, about 89 g) was added until the pH value of the solution was less than 4 in order to dissolve the solid particles. Ethyl acetate (2040 g) was added slowly to the mixture. The mixture was cooled to 0~10° C. and stirred at this temperature for 1 hour. The solid particles were filtered and washed with cooled ethyl acetate (420 g). The wet cake was dried in vacuum to give 160 g of irinotecan hydrochloride trihydrate form IV.

The invention is not limited by the embodiments described above which are presented as examples only but can be modified in various ways within the scope of protection defined by the appended patent claims.

We claim:

1. A crystalline form of irinotecan hydrochloride having a powder X-ray diffraction pattern with peaks at 20.3956±0.2, 22.2950±0.2, 12.0744±0.2, 8.4800±0.2, and 11.8306±0.2 degrees in two theta.

2. The crystalline form of irinotecan hydrochloride of claim 1 wherein the powder X-ray diffraction pattern further has peaks at 15.7587±0.2, and 18.5200±0.2 degrees in two theta.

3. The crystalline form of irinotecan hydrochloride of claim 1 having an infrared diffuse-reflectance pattern with peaks at approximately 1749, 1189, 1234, 1663, and 1720 wavenumbers.

4. The crystalline form of irinotecan hydrochloride of claim 1 wherein the X-ray diffraction pattern is substantially in accordance with that shown in FIG. 3.

5. The crystalline form of irinotecan hydrochloride of claim 1 having an infrared diffuse-reflectance pattern substantially in accordance with that shown in FIG. 4.

6. A process for preparing the crystalline form of irinotecan hydrochloride of claim 1 comprising:
   a) dissolving irinotecan in ethanol and hydrochloric acid,
   b) crystallizing irinotecan hydrochloride from the ethanol and hydrochloric acid to produce the crystalline form of claim 1, and
   c) separating the crystalline form of irinotecan hydrochloride from the ethanol and hydrochloric acid.

7. A crystalline form of irinotecan hydrochloride having a powder X-ray diffraction pattern with peaks at 23.9600±0.2, 20.9200±0.2, and 21.0800±0.2 degrees in two theta.

8. The crystalline form of irinotecan hydrochloride of claim 7 wherein the powder X-ray diffraction pattern further has peaks at 21.0944±0.2, 23.8375±0.2, 24.3200±0.2, and 10.2800±0.2 degrees in two theta.

9. The crystalline form of irinotecan of claim 7 having an infrared diffuse reflectance pattern with peaks at approximately 1229, 1721, 1190, 1659, and 1598 wavenumbers.

10. The crystalline form of irinotecan hydrochloride of claim 7 wherein the X-ray diffraction pattern is substantially in accordance with that shown in FIG. 5.

11. The crystalline form of irinotecan hydrochloride of claim 7 having an infrared diffuse-reflectance pattern substantially in accordance with that shown in FIG. 6.

12. A process for preparing the crystalline form of irinotecan hydrochloride of claim 7 comprising:
   a) dissolving irinotecan in methanol, ethyl acetate, and hydrochloric acid,
   b) crystallizing irinotecan hydrochloride from the methanol, ethyl acetate, and hydrochloric acid to produce the crystalline form of claim 7, and
   c) separating the crystalline form of irinotecan hydrochloride from the methanol, ethyl acetate, and hydrochloric acid.

13. A process for preparing a crystalline form of irinotecan hydrochloride comprising:
   a) dissolving irinotecan in ethanol, N-heptane, and hydrochloric acid, b) crystallizing irinotecan hydrochloride from the ethanol, N-heptane, and hydrochloric acid to produce the crystalline form, and c) separating the crystalline form of irinotecan hydrochloride from the ethanol, N-heptane, and hydrochloric acid; wherein the crystalline form of irinotecan hydrochloride has a powder X-ray diffraction pattern with peaks at 12.3406±0.2, 24.7913±0.2, 10.9438±0.2, 8.2056±0.2, 27.6750±0.2, 22.7206±0.2, and 21.2350±0.2 degrees in two theta.

14. The process of claim 13 wherein the crystalline form of irinotecan hydrochloride has an infrared diffuse-reflectance pattern with peaks at approximately 1686, 1612, 1748, 1192, and 1663 wavenumbers.

15. The process of claim 13 wherein the X-ray diffraction pattern is substantially in accordance with that shown in FIG. 1.

16. The process of claim 13 wherein the crystalline form of irinotecan hydrochloride has an infrared diffuse-reflectance pattern substantially in accordance with that shown in FIG. 2.

17. A process for preparing a crystalline form of irinotecan hydrochloride comprising:

a) dissolving irinotecan in ethanol, ethyl acetate, and hydrochloric acid, b) crystallizing irinotecan hydrochloride from the ethanol, ethyl acetate, and hydrochloric acid to produce the crystalline form, and c) separating the crystalline form of irinotecan hydrochloride from the ethanol, ethyl acetate, and hydrochloric acid; wherein the crystalline form of irinotecan hydrochloride has a powder X-ray diffraction pattern with peaks at 9.1912±0.2, 9.9800±0.2, 18.8937±0.2, 15.2725±0.2, 16.1681±0.2, 25.7400±0.2, and 27.0662±0.2 degrees in two theta.

18. The process of claim 17 wherein the crystalline form of irinotecan hydrochloride has an infrared diffuse reflectance pattern with peaks at 1712, 1231, 1188, 1668, and 1432 wavenumbers.

19. The process of claim 17 wherein the X-ray diffraction pattern is substantially in accordance with that shown in FIG. 7.

20. The process of claim 17 wherein the crystalline form of irinotecan hydrochloride has an infrared diffuse-reflectance pattern substantially in accordance with that shown in FIG. 8.

* * * * *